United States Patent [19]
Saermark et al.

[11] Patent Number: 5,770,688
[45] Date of Patent: Jun. 23, 1998

[54] METHOD AND COMPOSITION FOR THE TREATMENT OF MAMMALIAN HIV INFECTION

[75] Inventors: Torben Saermark, Malmo, Sweden; Volker Erfle, Munich, Germany

[73] Assignee: GSF-Forschungszentrum für Umwelt und Gesundheit GmbH, Oberschleissheim, Germany

[21] Appl. No.: 467,623

[22] Filed: Jun. 6, 1995

Related U.S. Application Data

[63] Continuation of Ser. No. 33,200, Mar. 16, 1993, abandoned, which is a continuation-in-part of Ser. No. 625,677, Dec. 7, 1990, abandoned.

[30] Foreign Application Priority Data

Dec. 7, 1989 [DE] Germany .......................... 39 40 526.5

[51] Int. Cl.$^6$ .................................................. A67K 38/16
[52] U.S. Cl. ........................................... 530/324; 514/12
[58] Field of Search ............................... 514/12; 530/324

[56] References Cited

U.S. PATENT DOCUMENTS 4,822,608  4/1989  Benton ...................................... 424/98

FOREIGN PATENT DOCUMENTS 0504191  8/1994  European Pat. Off. ....... A61K 37/02

OTHER PUBLICATIONS

Egberink et al., Suppression of Feline Immunodeficiency Virus Infection in vivo by 9–(2–phosphonomethoxyethyl)adenine, Proc. natl. Acad. Sci. USA, vol. 87, 3087–3091, 3087 (1990).
Kindt et al, Animal Models for Acquired Immunodeficiency Syndrome, Advances in Immunology, vol. 52, 425–474, 441 (1992).
Mellors, John W., Closing in on Human Immunodeficiency Virus–1, Nature Medicine, vol. 2, No. 3, 274–275 (1996).
Bendinelli et al. 1995. Feline Immunodeficiency Virus: A Interesting Model for Aids Studies & An Important Cat Pathogen. Clin Microbiol. Rev. 8(1):pp. 87–112.
H. Andreassen et al., "Analysis of the Secondary Structure of the Human Immunodeficiency Virus (HIV) Proteins p17, gp120, and gp41 by Computer Modeling Based on Neutral Network Methods," Journal of Acquired Immune Deficiency Syndromes, v. 3 (1990), pp. 615–622.
A. Argiolas et al., "Bombolitins, a New Class of Mast Cell Degranulating Peptides from the Venom of the Bumblebee Megabombus pennsylvanicus," The Journal of Biological Chemistry, v. 260, No. 3 (Feb. 10, 1985), pp. 1437–1444.
A. W. Bernheimer et al., "Interactions between membranes and cytolytic peptides," Biochimica et Biophysica Acta, v. ;864 (1986), pp. 123–141.
L. R. Boone et al., "Viral DNA Synthesized In Vitro by Avian Retrovirus Particles Permeabilized with Melittin," Journal of Virology, v. 37, No. 1 (Jan. 1918), pp. 109–116.
A. F. Esser et al., "Disassembly of viral membranes by complement independent of channel formation," Proc. Natl. Acad. Sci. USA, v. 76, No. 11 (Nov. 1979), pp. 5843–5847.
E. T. Kaiser et al., "Amphiphilic Secondary Structure: Design of Peptide Hormones," Science, v. 223 (20 Jan. 1984), pp. 249–255.
E. T. Kasier et al., "Secondary structures of proteins and peptides in amphiphilic environments (A Review)," Proc. Natl. Acad. Sci. USA, v. 80 (Feb. 1983), pp. 1137–1143.
K. Lubke et al., "Haemolytic Activity and Action on the Surface Tension of Aqueous Solutions of Synthetic Melittins and their Derivatives," Experentia, v. 27, No. 7 (1971), pp. 764–767.
W. Mellert et al., "HTLV–III/LAV—Antikorpertest: Indirekte Immunperoxidasefarbung (HILV–III/LAV antibody test: Indirect Immunoperoxidase staining)," AIDS—For Schung (AIFO) Feb. 1986 Heft 2, pp. 105–107.
W. Mellert et al., "Infection of human fibroblasts and osteoblast–like cells with HIV–1", AIDS, v. 4, No. 6 (1990), pp. 527–535.
T. Mosmann, "Rapid Colorimetric Assay for Cellular Growth and Survival: Application to Proliferation and Cytotoxicity Assays," Journal of Immunological Methods, v. 65 (1983), pp. 55–63.
T. Saermark et al., "Acylation of HIV proteins," Biochemical Society Transactions, v. 17 (1989), pp. 869–871.
Wachinger et al. FEBS vol. 309(3) 235–241.
ASM News vol. 56 No. 7 Jul. 1990.
Richman et al., J. of Virology, vol. 68, No. 3, Mar. 1994 pp. 1660–1666.
Saag et al., J. of Acquired Immune Deficiency Syndromes, F. Suppl. 2, S2–S11. (1994).
Carosi, AIDS, (1994) vol. 8, (Suppl. 3) S1–S2.
Leff, BioWorld Today, (Oct. 18, 1994) vol. 5, No. 210, pp. 1 & 5.
D. J. Witt et al., "Phosphorylation of Vesicular Stomatitis Virus Proteins as a Possible Contributing Factor in Virion Uncoating," J. gen. Virol., v. 56 (1981), pp. 383–391.
The Declaration of Release relates to the deposit of human mesenchymal cell line LC5 and LC5–HIV which were deposited with the German Patent Office and given accession No. I842 and I843 on Mar. 9, 1989. These cell lines were first mentioned in German Patent Application No. P 3916251.6.
The formulation of RPMI 1640 is set forth therein. RMPI 1640 is the culture upon which cell line LC5 and LC5–HIV were grown.
The Biomek 1000 advertisement relates to an automated laboratory workstation manufactured by Beckman Instruments and which was employed in the studies discussed in the present case.

Primary Examiner—Cecilia Tsang
Assistant Examiner—Anish Gupta
Attorney, Agent, or Firm—The Firm of Gordon W. Hueschen

[57] ABSTRACT

A method and composition are described for the treatment of mammalian HIV infections including administering an effective subtoxic dosage of melittin (Seq. ID NO:1) to the mammal whereby the growth of HIV infected cells or the replication of the virus in the infected cells of the mammal is inhibited.

10 Claims, 37 Drawing Sheets

Hymenoptera venoms. Prolonged toxicity studies – mice.

Body weight grams (g)
Group mean data

| Group | Sex | Body weight (g) at days after onset of dosing | | | | | | | | | | | | |
|---|---|---|---|---|---|---|---|---|---|---|---|---|---|---|
| | | 0 | 4 | 7 | 12 | 14 | 16 | 47 | 77 | 109 | 138 | 172 | autop. | 200-2C8 |
| Controls | ♂ | 31.4 | 31.4 | 32.0 | 32.2 | 32.6 | 32.2 | 35.0 | 31.6 | 36.2 | 36.4 | 36.2 | 37.0 | |
| " | ♀ | 24.8 | 24.6 | 25.0 | 25.4 | 26.0 | 25.2 | 27.8 | 28.0 | 29.6 | 29.8 | 31.6 | 31.6 | |
| Honey bee | ♂ | 30.4 | 30.4 | 31.0 | 31.8 | 31.4 | 31.2 | 33.2 | 33.2 | 36.0 | 37.4 | 36.4 | 36.2 | |
| " | ♀ | 24.4 | 24.2 | 24.8 | 25.0 | 25.4 | 25.0 | 27.6 | 27.8 | 29.0 | 28.4 | 29.8 | 31.0 | |
| Yellow Jacket | ♂ | 31.4 | 31.2 | 31.8 | 32.0 | 32.6 | 32.2 | 34.2 | 35.0 | 35.6 | 36.8 | 35.8 | 36.6 | |
| " | ♀ | 23.8 | 23.8 | 24.4 | 24.8 | 25.2 | 25.2 | 26.6 | 28.2 | 29.0 | 29.0 | 30.0 | 30.0 | |
| Hornet Mixture | ♂ | 33.2 | 33.8 | 34.0 | 34.4 | 34.6 | 35.2 | 37.4 | 37.0 | 38.2 | 38.4 | 37.6 | 38.8 | |
| " | ♀ | 24.6 | 24.6 | 24.8 | 25.2 | 25.4 | 25.4 | 28.0 | 28.2 | 28.6 | 28.4 | 28.8 | 29.8 | |
| Vespid Mixture | ♂ | 29.4 | 30.2 | 30.8 | 30.8 | 31.2 | 31.4 | 33.0 | 34.2 | 35.2 | 34.4 | 34.8 | 35.0 | |
| " | ♀ | 25.0 | 25.2 | 25.4 | 26.2 | 26.0 | 26.2 | 27.6 | 28.4 | 29.8 | 30.2 | 30.4 | 29.4 | |

FIG. 35

Hymenoptera venoms. Prolonged toxicity studies - mice.

Body weight grams (g)
Individual data

| Mouse No. | Substance | Sex | Body weight (g) at days after onset of dosing | | | | | | | | | | | |
|---|---|---|---|---|---|---|---|---|---|---|---|---|---|---|
| | | | 0 | 4 | 7 | 12 | 14 | 16 | 47 | 77 | 109 | 138 | 172 | (autopsy) 208 |
| 1 | Controls | ♂ | 29 | 29 | 30 | 31 | 31 | 31 | 37 | 33 | 35 | 34 | 34 | 35 |
| 2 | " | " | 31 | 31 | 31 | 31 | 31 | 31 | 32 | 33 | 36 | 37 | 36 | 35 |
| 3 | " | " | 35 | 35 | 36 | 36 | 37 | 36 | 37 | 33 | 35 | 35 | 35 | 39 |
| 4 | " | " | 29 | 29 | 30 | 29 | 29 | 29 | 32 | 34 | 36 | 37 | 37 | 38 |
| 5 | " | " | 33 | 33 | 33 | 34 | 35 | 34 | 37 | 35 | 39 | 39 | 39 | 38 |
| 6 | " | ♀ | 24 | 25 | 25 | 25 | 25 | 24 | 28 | 28 | 29 | 31 | 31 | 33 |
| 7 | " | " | 25 | 24 | 24 | 26 | 26 | 25 | 29 | 28 | 30 | 32 | 35 | 35 |
| 8 | " | " | 25 | 24 | 25 | 25 | 26 | 25 | 27 | 28 | 30 | 29 | 30 | 30 |
| 9 | " | " | 25 | 25 | 26 | 25 | 26 | 27 | 27 | 28 | 30 | 29 | 31 | 30 |
| 10 | " | " | 25 | 25 | 26 | 26 | 27 | 27 | 28 | 28 | 29 | 28 | 31 | 30 |

FIG.36

Hymenoptera venoms. Prolonged toxicity studies - mice.

Body weight grams (g)
Individual data

| Mouse No. | Substance | Sex | Body weight (g) at days after onset of dosing |||||||||||
|---|---|---|---|---|---|---|---|---|---|---|---|---|---|
| | | | 0 | 4 | 7 | 12 | 14 | 16 | 47 | 77 | 109 | 138 | 172 | (autopsy) 200-4 |
| 101 | Honey bee | ♂ | 29 | 29 | 29 | 30 | 29 | 29 | 31 | 31 | 34 | 34 | 33 | 35 |
| 102 | " | " | 32 | 32 | 32 | 33 | 31 | 33 | 35 | 34 | 40 | 42 | 43 | 37 |
| 103 | " | " | 31 | 31 | 32 | 33 | 32 | 32 | 33 | 33 | 34 | 35 | 32 | 34 |
| 104 | " | " | 30 | 30 | 31 | 31 | 31 | 30 | 32 | 32 | 33 | 35 | 36 | 36 |
| 105 | " | " | 30 | 30 | 31 | 32 | 32 | 32 | 35 | 36 | 39 | 41 | 38 | 39 |
| 106 | " | ♀ | 24 | 23 | 24 | 24 | 25 | 25 | 28 | 26 | 28 | 28 | 28 | 29 |
| 107 | " | " | 24 | 24 | 24 | 25 | 26 | 25 | 27 | 27 | 28 | 28 | 30 | 29 |
| 108 | " | " | 24 | 27 | 25 | 25 | 24 | 24 | 27 | 28 | 28 | 27 | 28 | 31 |
| 109 | " | " | 26 | 27 | 26 | 27 | 27 | 26 | 30 | 32 | 33 | 31 | 33 | 32 |
| 110 | " | " | 24 | 24 | 25 | 24 | 25 | 25 | 26 | 26 | 28 | 28 | 30 | 34 |

FIG.37

Hymenoptera venoms. Prolonged toxicity studies - mice.

Body weight grams (g)
Individual data

| Mouse No. | Substance | Sex | Body weight (g) at days after onset of dosing | | | | | | | | | | | |
|---|---|---|---|---|---|---|---|---|---|---|---|---|---|---|
| | | | 0 | 4 | 7 | 12 | 14 | 16 | 47 | 77 | 109 | 138 | 172 | (autopsy) 201-4 |
| 201 | Yellow Jacket | ♂ | 34 | 34 | 35 | 35 | 36 | 35 | 38 | 39 | 40 | 40 | 37 | 38 |
| 202 | " | " | 30 | 30 | 30 | 30 | 31 | 31 | 33 | 35 | 35 | 36 | 36 | 35 |
| 203 | " | " | 32 | 32 | 32 | 33 | 33 | 33 | 33 | 33 | 35 | 37 | 37 | 39 |
| 204 | " | " | 31 | 31 | 32 | 32 | 33 | 33 | 35 | 35 | 34 | 37 | 38 | 37 |
| 205 | " | ♀ | 30 | 29 | 30 | 30 | 30 | 29 | 32 | 33 | 34 | 34 | 31 | 34 |
| 206 | " | " | 23 | 23 | 23 | 24 | 24 | 24 | 24 | 26 | 26 | 26 | 29 | 27 |
| 207 | " | " | 24 | 24 | 25 | 25 | 25 | 25 | 27 | 29 | 30 | 29 | 32 | 32 |
| 208 | " | " | 23 | 24 | 25 | 24 | 25 | 25 | 27 | 29 | 30 | 32 | 30 | 32 |
| 209 | " | " | 25 | 25 | 25 | 26 | 26 | 26 | 27 | 29 | 29 | 28 | 28 | 29 |
| 210 | " | " | 24 | 23 | 25 | 26 | 26 | 26 | 28 | 28 | 30 | 30 | 31 | 30 |

FIG.38

Hymenoptera venoms. Prolonged toxicity studies - mice.

Body weight grams (g)
Individual data

| Mouse No. | Substance | Sex | Body weight (g) at days after onset of dosing | | | | | | | | | | | (autopsy) |
|---|---|---|---|---|---|---|---|---|---|---|---|---|---|---|
| | | | 0 | 4 | 7 | 12 | 14 | 16 | 47 | 77 | 109 | 138 | 172 | 202-7 |
| 301 | Hornet mixture | ♂ | 34 | 35 | 35 | 35 | 36 | 36 | 39 | 39 | 42 | 40 | 38 | 40 |
| 302 | " | " | 30 | 31 | 31 | 32 | 32 | 33 | 34 | 34 | 33 | 36 | 36 | 36 |
| 303 | " | " | 34 | 34 | 35 | 35 | 35 | 36 | 36 | 34 | 36 | 35 | 37 | 39 |
| 304 | " | " | 32 | 33 | 33 | 33 | 34 | 34 | 38 | 38 | 38 | 43 | 40 | 39 |
| 305 | " | " | 36 | 36 | 36 | 37 | 36 | 37 | 40 | 40 | 42 | 38 | 37 | 40 |
| 306 | " | ♀ | 25 | 25 | 25 | 25 | 26 | 26 | 28 | 28 | 28 | 28 | 25 | 24 |
| 307 | " | " | 23 | 23 | 23 | 24 | 24 | 23 | 27 | 26 | 26 | 25 | 26 | 29 |
| 308 | " | " | 26 | 25 | 26 | 27 | 26 | 26 | 30 | 32 | 31 | 31 | 34 | 36 |
| 309 | " | " | 23 | 24 | 24 | 24 | 24 | 25 | 27 | 26 | 28 | 28 | 29 | 28 |
| 310 | " | " | 26 | 26 | 26 | 26 | 27 | 27 | 28 | 29 | 30 | 30 | 30 | 32 |

FIG.39

Hymenoptera venoms. Prolonged toxicity studies - mice.
Body weight grams (g)
Individual data

| Mouse No. | Substance | Sex | Body weight (g) at days after onset of dosing | | | | | | | | | | | | |
|---|---|---|---|---|---|---|---|---|---|---|---|---|---|---|---|
| | | | 0 | 4 | 7 | 12 | 14 | 16 | 47 | 77 | 109 | 138 | 172 | (autopsy) 202-7 |
| 401 | Vespid Mixture | ♂ | 29 | 30 | 29 | 30 | 30 | 31 | 31 | 32 | 35 | 36 | 36 | 35 |
| 402 | " | " | 27 | 27 | 28 | 28 | 28 | 28 | 30 | 31 | 32 | 32 | 33 | 32 |
| 403 | " | " | 30 | 31 | 32 | 31 | 32 | 31 | 34 | 36 | 37 | 33 | 33 | 34 |
| 404 | " | " | 30 | 31 | 32 | 32 | 33 | 33 | 35 | 37 | 37 | 37 | 38 | 39 |
| 405 | " | " | 31 | 32 | 33 | 33 | 33 | 34 | 35 | 35 | 35 | 34 | 34 | 35 |
| 406 | " | ♀ | 26 | 26 | 26 | 27 | 26 | 27 | 28 | 28 | 30 | 32 | 31 | 29 |
| 407 | " | " | 25 | 25 | 26 | 26 | 26 | 27 | 29 | 30 | 29 | 30 | 30 | 30 |
| 408 | " | " | 23 | 24 | 24 | 25 | 25 | 25 | 25 | 27 | 31 | 29 | 29 | 28 |
| 409 | " | " | 25 | 25 | 25 | 27 | 26 | 26 | 28 | 29 | 29 | 31 | 31 | 31 |
| 410 | " | " | 26 | 26 | 26 | 26 | 27 | 26 | 28 | 28 | 30 | 29 | 31 | 29 |

Hymenoptera venoms. Prolonged toxicity studies - mice.

Legends for Fig. 41.

1. Focally small accumulations of lymphoid cells.

2. A small adenoma, probably originating from bronchial epithelium.

3. A small nodular hyperplasia of bronchial epithelium.

4. A small, oldish and indistinct necrosis with infiltrations of polymorphonuclear granulocytes.

5. Focally oldish necroses with heavy infiltration of polymorphs.

6. Widespread and indistinct oldish necroses with infiltration of numerous polymorphs.

7. A moderately lymphoid hyperplasia.

8. Necrosis of a few liver cells with slight cellular infiltration.

9. A focal necrosis, slightly demarcated by fibrous tissue and strongly infiltrated with polymorphs and macrophages.

10. A slight chronic pyelonephritis.

11. A chronic fibrous adhesion to the abdominal wall.

12. A chronic fibrous and well vascularized adhesion to the pancreas.

FIG.41A

Melittin analogues and other peptides used:

1. Melittin:

Sequence: Gly-Ile-Gly-Ala-Val-Leu-Lys-Val-Leu-Thr-Thr-Gly-Leu-Pro-Ala-Leu-Ile-Ser-Trp-Ile-Lys-Arg-Lys-Arg-Gln-Gln-Amide.

2. Melittin acid:

Sequence: Gly-Ile-Gly-Ala-Val-Leu-Lys-Val-Leu-Thr-Thr-Gly-Leu-Pro-Ala-Leu-Ile-Ser-Trp-Ile-Lys-Arg-Lys-Arg-Gln-Gln-Acid.

3. Melittin 6:

Sequence: Gly-Ile-Gly-Ala-Val-Leu-Lys-Val-Leu-Thr-Thr-Gly-Leu-Pro-Ala-Leu-Ile-Ser-Trp-Ile-Lys-Lys-Lys-Lys-Gln-Gln-Amide.

4. Melittin 4:

Sequence: Gly-Ile-Gly-Ala-Val-Leu-Lys-Val-Leu-Thr-Thr-Gly-Leu-Pro-Ala-Leu-Ile-Ser-Trp-Ile-Lys-Arg-Lys-Arg-Gly-Gly-Amide.

5. Melittin E:

Sequence: Gly-Ile-Gly-Ala-Val-Leu-Lys-Val-Leu-Thr-Thr-Gly-Leu-Pro-Ala-Leu-Ile-Ser-Trp-Ile-Gly-Gly-Gly-Gly-Gly-Gly-Amide.

6. Melittin F:

Sequence: Gly-Ile-Gly-Ala-Val-Leu-Lys-Val-Leu-Thr-Thr-Gly-Leu-Pro-Ala-Ile-Ser-Trp-Ile-Orn-Orn-Amide.

7. Melittin 1-20:

Sequence: Gly-Ile-Gly-Ala-Val-Leu-Lys-Val-Leu-Thr-Thr-Gly-Leu-Pro-Ala-Ile-Ser-Trp-Ile-Amide.

8. Amfi 1:

Sequence: Gly-Thr-Asp-Arg-Val-Ile-Glu-Val-Val-Gln-Gly-Ala-Cys-Arg-Ala-Ile-Arg-His-Ile-Pro-Arg-Arg-Ile-Arg-Gln-Gly-Amide.

9. Amfi 2:

Sequence: Gly-Gln-Arg-Val-Arg-Asn-Val-Ile-Ser-Leu-Val-Ala-Phe-Val-Ile-Arg-Leu-Gly-Val-Leu-Gly-Gly-Val-Ile-Met-Ile-Phe-Amide.

10. MHC:

Sequence: Val-Ala-Ala-Lys-Ala-Asn-Arg-Val-Ala-Asp-Glu-Ile-Arg-His-Lys-Arg-Glu-Lys-Leu-Glu-Amide.

11. Holst:

Sequence: Phe-Ala-Glu-Ser-Gly-Val-Asp-Thr-Pro-Val-Phe-Asn-Ser-Tyr-Amide.

| Group | Number | RLV | Melittin (i.p.) | Body weight (g) | Spleen weight (g) | Inhibition (%) |
|---|---|---|---|---|---|---|
| 1 | 4 | - | - | 23.6±1.3 | 0.15±0.01 | |
| 2 | 4 | - | - | 23.3±1.7 | 0.15±0.01 | |
| 3 | 6 | - | + | 22±1.4 | 0.16±0.03 | |
| 4 | 6 | + | + | 23.5±1.5 | 0.14±0.02 | |
| 5 | 6 | + | - | 21.9±1.7 | 2.3±0.61 | |
| 6 | 6 | + | + | 21.3±0.7 | 0.4±0.35 | 82 |
| 7 | 6 | + | + | 23.1±0.8 | 1.2±0.99 | 48 |
| 8 | 6 | + | + | 23.5±0.5 | 1.5±0.96 | 34 |
| 9 | 6 | + | + | 22.8±0.9 | 1.6±0.55 | 29 |
| 10 | 6 | + | + | 24.5±0.6 | 2.1±0.37 | 7 |

Group 1: No infection; no treatment; Sacrifice day 14
Group 2: No infection; no treatment; Sacrifice day 21
Group 3: Treatment with Melittin at days -1, 1, 4, 8, 12; Sacrifice day 14
Group 4: Treatment with Melittin at days -1, 1, 4, 8, 12, 16, 20; Sacrifice day 21
Group 5: Infection with RLV; Sacrifice day 21
Group 6: Infection with RLV; Treatment with Melittin at days -1, 1, 4, 8, 12, 16, 20; Sacrifice day 21
Group 7: Infection with RLV; Treatment with Melittin at days 1, 4, 8, 12, 16, 20; Sacrifice day 21
Group 8: Infection with RLV; Treatment with Melittin at days 8, 12, 16, 20; Sacrifice day 21
Group 9: Infection with RLV; Treatment with Melittin at days 14, 16, 18, 20; Sacrifice day 21
Group 10: Infection with RLV; Treatment with Melittin at days 1, 8, 14; Sacrifice day 21

FIG. 44

| Group | Number | RLV | Melittin (i.p.) | Body weight (g) | Spleen weight (g) | Inhibition (%) |
|-------|--------|-----|-----------------|-----------------|-------------------|----------------|
| 1 | 6 | + | + | 24.5±2.22 | 1.1±0.81 | 56 |
| 2 | 6 | + | + | 23.7±0.58 | 1.3±0.67 | 48 |
| 3 | 6 | + | + | 24.1±0.88 | 1.1±0.7 | 56 |
| 4 | 6 | + | − | 24.6±1.93 | 2.3±0.45 | |
| 5 | 6 | + | − | 24.7±1.34 | 2.7±1.14 | |
| 6 | 6 | + | + | 23.6±1.57 | 1.1±1.21 | 56 |
| 7 | 6 | + | + | 22.6±1.5 | 0.7±0.86 | 72 |
| 8 | 6 | + | + | 24.3±1.39 | 0.9±1.12 | 64 |

Group 1: Infection with RLV; Treatment with Melittin at days 4, 8, 12, 16, 20; Sacrifice day 21
Group 2: Infection with RLV; Treatment with Melittin at days 2, 4, 6, 8, 10, 12, 14, 16, 18, 20; Sacrifice day 21
Group 3: Infection with RLV; Treatment with Melittin every day; Sacrifice day 21
Group 4: Infection with RLV; Sacrifice day 21
Group 5: Infection with RLV; Sacrifice day 21
Group 6: Infection with RLV; Treatment with Melittin 12 hours before infection; Sacrifice day 21
Group 7: Infection with RLV; Treatment with Melittin 24 hours before infection; Sacrifice day 21
Group 8: Infection with RLV; Treatment with Melittin 6 hours before infection; Sacrifice day 21

FIG. 45

| Group | Number | RLV | Melittin (i.p.) | Body weight (g) | Spleen weight (g) | Inhibition (%) |
|---|---|---|---|---|---|---|
| 1 | 14 | + | − | 23.1±2.82 | 2.8±0.9 | |
| 2 | 10 | + | + | 25.4±0.68 | 1.4±0.72 | 50 |
| 3 | 10 | + | + | 26.1±1.2 | 1.5±0.65 | 46 |
| 4 | 10 | + | + | 25.9±2.27 | 1.5±0.62 | 46 |
| 5 | 10 | + | + | 26.7±1.03 | 1.3±0.77 | 54 |

Group 1: Infection with RLV; Sacrifice day 21
Group 2: Infection with RLV; Treatment with Melittin at days −5, −4, −3, −2, −1; Sacrifice day 21
Group 3: Infection with RLV; Treatment with Melittin at days −4, −3, −2, −1; Sacrifice day 21
Group 4: Infection with RLV; Treatment with Melittin at days −5, −3, −1; Sacrifice day 21
Group 5: Infection with RLV; Treatment with Melittin at days −1, 4, 8, 12, 16, 20; Sacrifice day 21

FIG.46

| Group | Number | RLV | Melittin (i.p.) | Body weight (g) | Spleen weight (g) | Inhibition (%) |
|---|---|---|---|---|---|---|
| 1 | 10 | + | – | 23.2±1.5 | 0.13±0.01 | |
| 2 | 10 | + | + | 23.3±0.93 | 0.15±0.04 | |
| 3 | 10 | + | – | 25.9±1.47 | 0.3±0.09 | |
| 4 | 10 | + | + | 24.3±1.6 | 0.2±0.04 | 33 |
| 5 | 10 | + | – | 25.8±1.32 | 0.6±0.39 | |
| 6 | 10 | + | + | 25.37±1.3 | 0.4±0.28 | 33 |
| 7 | 10 | + | – | 26.9±2.04 | 1.7±0.73 | |
| 8 | 10 | + | + | 25.8±1.84 | 1.2±0.7 | 29 |

Group 1: Infection with RLV; Sacrifice day 5
Group 2: Infection with RLV; Treatment with Melittin at days −5, −4, −3, −2, −1, 1, 4; Sacrifice day 5
Group 3: Infection with RLV; Sacrifice day 10
Group 4: Infection with RLV; Treatment with Melittin at days −5, −4, −3, −2, −1, 1, 4, 8; Sacrifice day 10
Group 5: Infection with RLV; Sacrifice day 15
Group 6: Infection with RLV; Treatment with Melittin at days −5, −4, −3, −2, −1, 1, 4, 8, 12; Sacrifice day 15
Group 7: Infection with RLV; Sacrifice day 21
Group 8: Infection with RLV; Treatment with Melittin at days −5, −4, −3, −2, −1, 1, 4, 8, 12, 16, 20; Sacrifice day 21

FIG. 47A

| Sample dilution | 1:1000 | | | | 1:100000 | | | | 1:100000 | | | |
|---|---|---|---|---|---|---|---|---|---|---|---|---|
| Amplification cycles | 25 | 20 | 15 | 10 | 25 | 20 | 15 | 10 | 25 | 20 | 15 | 10 |
| Optical density | 66 | 69 | 39 | 8 | 75 | 62 | 33 | 1 | 72 | 40 | 4 | 0 |

FIG. 47B

Cat M

| day 1 | | | | day 14 | | | | day 28 | | | | day 42 | | | | day 56 | | | | day 116 | | | |
|---|---|---|---|---|---|---|---|---|---|---|---|---|---|---|---|---|---|---|---|---|---|---|---|
| 25 | 20 | 15 | 10 | 25 | 20 | 15 | 10 | 25 | 20 | 15 | 10 | 25 | 20 | 15 | 10 | 25 | 20 | 15 | 10 | 25 | 20 | 15 | 10 |
| 57 | 43 | 9 | 0 | 80 | 15 | 17 | 0 | 82 | 48 | 14 | 0 | 79 | 56 | 16 | 0 | 56 | 43 | 7 | 0 | 47 | 19 | 2 | 0 |

FIG. 47C

Cat G

| day 1 | | | | day 14 | | | | day 28 | | | | day 42 | | | | day 56 | | | | day 116 | | | |
|---|---|---|---|---|---|---|---|---|---|---|---|---|---|---|---|---|---|---|---|---|---|---|---|
| 25 | 20 | 15 | 10 | 25 | 20 | 15 | 10 | 25 | 20 | 15 | 10 | 25 | 20 | 15 | 10 | 25 | 20 | 15 | 10 | 25 | 20 | 15 | 10 |
| 62 | 47 | 21 | 1 | 68 | 64 | 16 | 1 | 69 | 45 | 10 | 1 | 60 | 11 | 1 | 1 | 70 | 41 | 3 | 0 | 60 | 18 | 1 | 0 |

METHOD AND COMPOSITION FOR THE TREATMENT OF MAMMALIAN HIV INFECTION

The present application is a continuation of our prior-filed application Ser. No. 08/033,200, filed Mar. 16, 1993, now abandoned, which in turn is a continuation-in-part of 07/625,677, filed Dec. 7, 1990, now abandoned.

BACKGROUND OF THE INVENTION

1. Field of the Invention

The present invention relates to a method and composition for the treatment of mammalian HIV infections, and more particularly to such a method and composition for treating mammalian HIV infections and which employs hymenoptera venom, or proteinaceous or polypeptide components thereof and which is introduced into the mammalian hosts and which are individually operable to restrict or substantially inhibit the virus replication in the HIV infected cells of the mammal.

2. Description of the Prior Art

The medical profession has long sought an effective method and composition for the treatment of HIV infected individuals. As herein intended, an HIV infection is meant to encompass both HIV1 and HIV2 infections. In this regard, the present research has been directed to seeking a potentially useful therapeutic agent for combatting an HIV infection and wherein the composition may inhibit viral reproduction of HIV infected cells, but which does not have numerous deleterious side effects. More particularly, the purpose of such research is to find a composition which is an alternative treatment to the current use of AZT. The composition, however, must be operable to selectively destroy HIV infected, or alternatively HIV propagating cells, in an effort to contain or substantially limit the reservoir of available virus cells.

As should be understood, HIV viruses are retroviruses and are therefore most appropriately classified as RNA viruses. The RNA of these particular retroviruses, however, cannot be directly propagated by means of replicase, but rather require an intermediary of DNA synthesis, with the assistance of reverse transcriptase. As should be understood, the DNA serves as a template for the multiplication of the RNA virus. This DNA is later integrated into the host cell genome. This event of integration subsequently leads to the production of new virus cells.

The present invention, which utilizes subtoxic concentrations of hymenoptera venom or proteinaceous or polypeptide components thereof appears to interfere with virus replication at subtoxic concentrations by means of inhibiting reverse transcriptase, and/or selectively inhibiting the growth of HIV infected cells thereby substantially and therapeutically eliminating the virus reservoir with the numerous benefits attendant thereto.

U.S. Pat. No. 4,822,608 issued to Benton et al. on Apr. 18, 1989 and entitled "METHODS AND COMPOSITIONS FOR THE TREATMENT OF MAMMALIAN INFECTIONS EMPLOYING MEDICAMENTS COMPRISING HYMENOPTERA VENOM OR PROTEINACEOUS OR POLYPEPTIDE COMPONENTS THEREOF" teaches that secondary agents derived from nature such as hymenoptera venom or proteinaceous or polypeptide components thereof has a potentiating effect on antibacterial agents. This reference further suggests that such compositions may also have increased anti-viral, carcinostatic and anti-carcinogenic effects on various maladies. More particularly, the reference to Benton et al. discloses the use of melittin (Seq. ID NO:1) which is the main component of honey bee toxin, in combination with assorted antibiotic agent as having antibacterial activity against predetermined infections. Further this reference teaches that a synergistic benefit may be achieved by the combination of the melittin (Seq. ID NO:1) and assorted antibiotics in various therapeutically effective amounts.

As discussed in detail in the prior art reference to Benton et al., melittin (Seq. ID NO:1), the main component in honey bee toxin is a polypeptide which includes substantially 26 amino acid residues. These amino acid residues include, Gly-Ile-Gly-Ala-Val-Leu-Lys-Val-Leu-Thr-Thr-Gly-Leu-Pro-Ala-Leu-Ile-Ser-Trp-Ile-Lys-Arg-Lys-Arg-Gln-Gln-Amide. Moreover, the inventors have discovered a direct effect of melittin analogues and wherein at least the last six (C-terminal) amino acids are altered and replaced by six glycine residues appear to have a therapeutic benefit similar to melittin, these amino acid analogues having a structure of Gly-Ile-Gly-Ala-Val-Leu-Lys-Val-Leu-Thr-Thr-Gly-Leu-Pro-Ala-Leu-Ile-Ser-Trp-Ile-Gly-Gly-Gly-Gly-Gly-Gly (Seq. ID NO:5).

Therefore, it has long been known that it would be desirable to have a method and composition for treating HIV infected mammals in a safe and effective manner and which further avoids the detriments individually associated with conventional HIV therapy such as that attendant with AZT, but which is operable to eliminate or substantially diminish the reservoir of viral cells which may infect the mammal.

OBJECTS AND SUMMARY OF THE INVENTION

It is therefore an object of the present invention to provide an improved method and composition for the treatment of HIV infections in mammals and which employs hymenoptera venom, or proteinaceous, or polypeptide components thereof.

Another object of the present invention is to provide such a method and composition for the treatment of HIV infections in mammals and wherein the hymenoptera venom is selected from the group consisting essentially of honey bee venom, bumble bee venom, yellow jacket venom, and bald-face hornet venom, active protein components of said venom, active protein components of said venom and mixtures thereof.

Another object of the present invention is to provide such a method and composition for the treatment of HIV or other retroviral infections in mammals and wherein the method includes administering an effective subtoxic dosage of a structural analogue of melittin (Seq. ID NO:5) or melittin (Seq. ID NO:1) itself to the mammal whereby virus replication in the retroviral infected cells of the mammal is substantially inhibited, or growth of the retroviral infected cells is inhibited.

Another object of the present invention is to provide such a method and composition for the treatment of retroviral infections in mammals and wherein the method includes, administering an effective, subtoxic dosage of a polypeptide mixture of melittin, and structural analogues thereof to the mammal, whereby replication of viral cells in the retroviral infected cells are inhibited.

Further objects and advantages of the present invention are to provide an improved method and composition for the treatment of mammalian HIV or other retroviral infections which is safe and effective, and which further avoids the detriments individually associated with the prior art therapy for these same maladies.

BRIEF DESCRIPTION OF THE DRAWINGS

FIG. 35 is a graphic illustration which shows a prolonged toxicity study with mice, and more particularly the effective body weight of the mice as it relates to the various venoms which were used during the toxicity study and which were taken at various times after the onset of dosing with the particular venom.

FIG. 36 is a graphic illustration which shows the body weight of the mice in the prolonged toxicity study as a function of the number of days after the onset of dosing with the substance used in the toxicity study.

FIG. 37 is a graphic illustration which shows the body weight of individual mice as a function of the use of honey bee venom at various days after the onset of dosing.

FIG. 38 is a graphic illustration which shows the body weight of the mice as a function of the use of yellow jacket venom at various days after the onset of dosing.

FIG. 39 is a graphic illustration which shows the body weight of the mice as a function of the use of hornet mixture at various days after the onset of dosing.

FIG. 40 is a graphic illustration which shows the body weight of mice as a function of the use of a vespid mixture at various days after the onset of dosing.

FIG. 41 is a graphic illustration which shows a prolonged toxicity study for mice and which summarizes the microscopic examination of the various anatomical parts of the respective mice receiving the honey bee and yellow jacket mixture following the toxicity study.

FIG. 41A provides a legend for the various data presented in FIG. 40.

FIG. 42 is a graphic illustration of the structure of melittin (Seq. ID NO:1) and the structural analogues thereof.

FIG. 43 is a graphic illustration which compares the body weight, and spleen weight, of various groups of mice which have been utilized in a Rauscher leukemia virus model (RLV) study. This graphic illustration compares and contrast the body weight of the mice and the individual spleen weights on predetermined sacrifice dates.

FIG. 44 is a graphic illustration of various groups of mice which have been utilized in a Rauscher leukemia virus model (RLV) study and which compares and contrasts the body weights and spleen weights of the individual groups of mice at predetermined sacrifice dates, and under various administration intervals.

FIG. 45 is a graphic illustration which shows various groups of mice which have been utilized in a Rauscher leukemia virus model (RLV) study and which compares and contrasts the body weight, and spleen weight, of the individual groups of mice at predetermined sacrifice dates.

FIG. 46 is a graphic illustration of several groups of mice which are utilized in a Rauscher leukemia virus model (RLV) study and which compares and contrasts the body weights and spleen weights of the individual groups of mice at predetermined sacrifice dates.

FIGS. 47A, B and C compares and contrasts the intensity of the bands of UV light exposures following quantitative PCR.

DESCRIPTION OF THE PREFERRED EMBODIMENT MATERIALS AND METHODS

Materials

Figure 1:
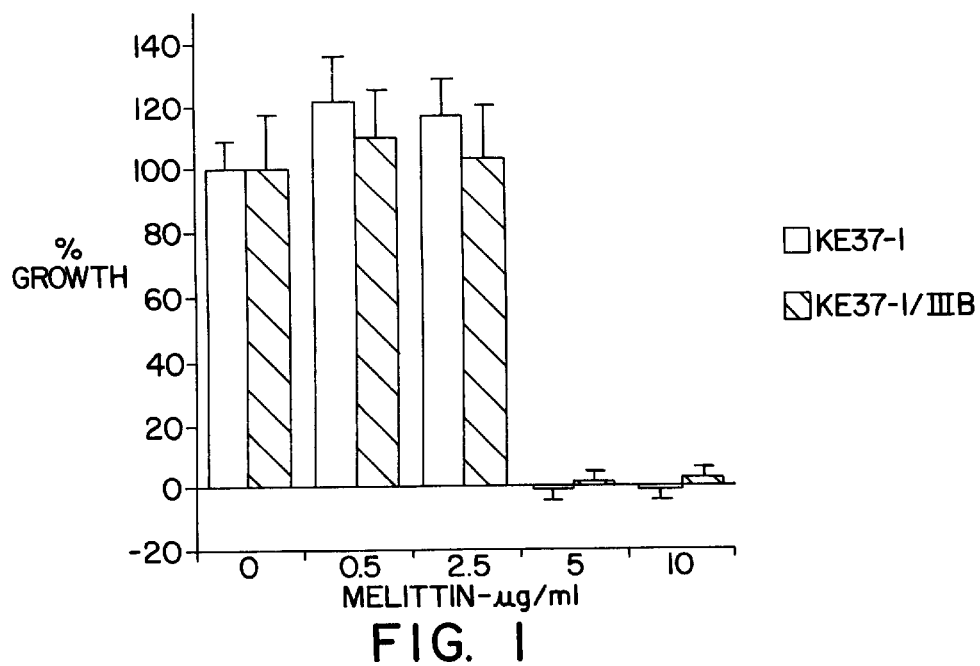
FIG. 1 is a graphic illustration which shows a comparison of cell growth achieved with non-infected and HIV infected cells as a percentage of untreated controls and which are interdependent with the melittin (Seq. ID NO:1) concentration.
Figure 2:
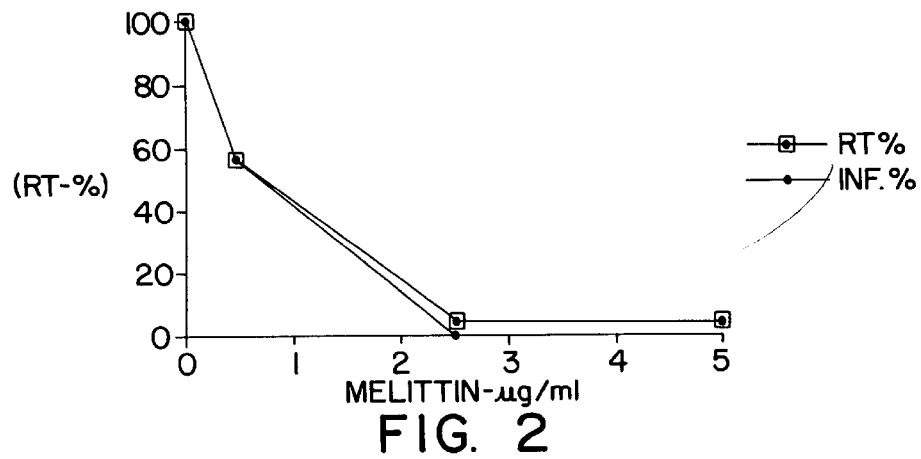
FIG. 2 is a graphic illustration which shows the activity of reverse transcriptase (RT%) as compared with a standardized cell line, and as further compared with the infectivity (INF%) of the culture supernatant of HIV infected T-lymphoma cells (KE37-1/111β) as a percentage of untreated controls and which are interdependent with the concentration of melittin (Seq. ID NO:1).

The KE37-1 (uninfected) and KE37-1/111β (infected) cell lines discussed below are commercially available from the Dr. Robert Gallows Laboratory of the NIH in the United States of America and grown in a medium of RPMI 1640 (GIBCO) and further supplemented with 10% fetal calf serum which contained approximately 100 units of penicillin, 100 μg streptomycin, and approximately 0.25 μg fungizone (Amphotericin B) per milliliter. The human mesenchymal cell lines LC5 and LC5-HIV, discussed below, are deposited with the Collection De L'Institut Pasteur of Paris, France on Mar. 9, 1989 and given the accession numbers I-842 and I-843, respectively. The LC5 and LC5-HIV cell lines were grown in a medium of RPMI 1640 and supplemented with 10% fetal calf serum.

Synthetic Peptides

The melittin peptides (Seq. ID NO:1) and analogues from GP41 were synthesized using a commercially available peptide synthesizer (model Biolynx, Pharmacia Biochrome, Cambridge UK) and the preweighted amino acid OPFP esters supplied for this machine (Pharmacia Biochrome, Cambridge, UK). The synthesis strategy was based on the Fmoc strategy as described in the manual for the equipment. The acylation rate was monitored by the Bioplus software using the release of anionic dye (Acid violet 17, 30 mg pr 100 ml dimethylformamide and 0,14 ml diisopropylethylamine) at 600 nm according to the protocol supplied by the manufacturer. The principle is known as counter ion distribution monitoring, CDM, and is described by Salisbury, S. A., Treemeer, E. J., Davies, J. W. and Owen, D.,E.,I.,A., (1990) J. Chem. Soc., Chem. Commun., 1990, p. 538–540. The linkers used resulted in release of peptide amide (Ultrosyn C, Pharmacia Biochrome, Cambridge, UK).

The first coupling to the acid labile linker Ultrosyn C (0.1 meq) was carried out using a symmetrical anhydride (0.4 mcq) and addition of dimethylaminopyridine (0.05 meq). This resulted in at least 80% coupling after 1 hour as determined by release of the Fmoc group and untreated sites were capped using acetic anhydride. The subsequent couplings were carried out using commercially available active esters (Pharmacia Biochrome, UK) with a coupling time determined by the CDM carried out automatically by the software used (above). Typical coupling times were typically 1 hour using 4 times excess of the esters. Ser was coupled using dihydroxybenzotriazole esters until colourless (1.5–2 h). The Fmoc group was removed by 5 bed volumes of piperidine (20% in dimethylformamide). The dimethylformamide was distilled before use and essentially amine free as determined by the dinitrofluorobenzene test as described by the protocol for the Biolynx. None of the couplings offered particular problems and the crude peptides appeared more than 80% pure as determined by high pressure liquid chromatography (HPLC, see below).

The peptides were cleaved from the resin using trifluoroacetic acid with the addition of 2% anisole and 2% ethanedithiol for 2 hours followed by ether precipitation. The peptide was purified to more than 95% purity by HPLC on a TSK 120T reverse phase column (7.5×300 mm) (Pharmacia, Sweden). The peptides typically eluded at 65% acetonitrile (between 55 and 75%) using a linear gradient over 90 minutes from 0 to 80% acetonitrile in 0.1% trifluoroacetic acid. The sequence was verified by protein sequencing on an Applied Biosystem sequencer according to the manufacturer.

The synthesis of GP41 analogues and mastoparan were carried out as described for the melittins. A listing of the melittin analogues and other peptides used is depicted in FIG. 42.

Method

Referring more particularly to FIGS. 1–4, melittin (Seq. ID NO:1) and its specified analogues were tested for their effect on HIV-infected T-lymphoma cells. In this regard the following cell lines were employed in the testing: KE37-1 (uninfected) and KE37-1/111S (infected with HTLV-111β). These infected cells were incubated for a period of seven days under test conditions at a temperature of 37° C. and in the presence of 5% $CO_2$. A culture medium of RPMI 1640 (GIBCO) was employed and was further supplemented with 10% fetal calf serum which contained approximately 100 units of penicillin, 100μ of streptomycin, and approximately 0.25μ fungizone (Amphotericin B) per milliliter. This equals 1 milliliter of antibiotic-antimycotic solution (GIBCO Catalogue No. 043-05240 per 100 ml. of medium.) After a one week incubation period in the presence of various concentrations of the above-identified substances, which were added fresh daily to the medium, the following tests were carried out with the cultures. A first test was conducted for purposes of determining the relative cell concentration as a function of the number of HIV infected cells present by employing an MTT test. The MTT test was carried out in microtiter plates according to T. Mosmann, "Rapid Colorimetric Assay for Cellular Growth and Survival: Application to Proliferation and Cytotoxicity Assays," *Journal of Immunological Methods*, v. 65 (1983), pp. 55–63. The MTT test was slightly modified: 10 μl of an MTT solution (5 mg/ml MTT dissolved in PBS, sterilized by filtration; MTT is 3-(4,5-Dimethylthiazole-2-yl)-2,5-diphenyltetrazolimbromide) were added to every well. The cells were incubated with MTT for four hours at 37° in 5% $CO_2$, atmosphere. The yellow MTT is reduced to a blue formazane by metabolically active cells. The reaction was stopped by adding 200μ of 0.04N HCl in isopropanol to every well and the dye was extracted. The resulting solutions were vigorously mixed in order to dissolve all the formazene crystals. The optical density (OD) of the solution was determined at=600 nm. The optical density is proportional to the cell density under these conditions.

The second test was conducted to determine the activity of reverse transcriptase in the supernatant of treated, HIV infected cell culture, by employing the test described by Poiesz et al. and which is found at PNAS 77 (1980): 1415–1419 and which was subsequently modified. A third test was conducted for purposes of determining the relative infectious nature of the supernatant of treated, HIV infected cell cultures. In this regard, uninfected, HIV receptive human embryonal lung cells (LC5) were incubated in the culture supernatant which was to be tested, and this was subsequently followed by a three day cultivation of the same cells in fresh media. These cells were then tested for the production of HIV specific proteins.

Figure 3:
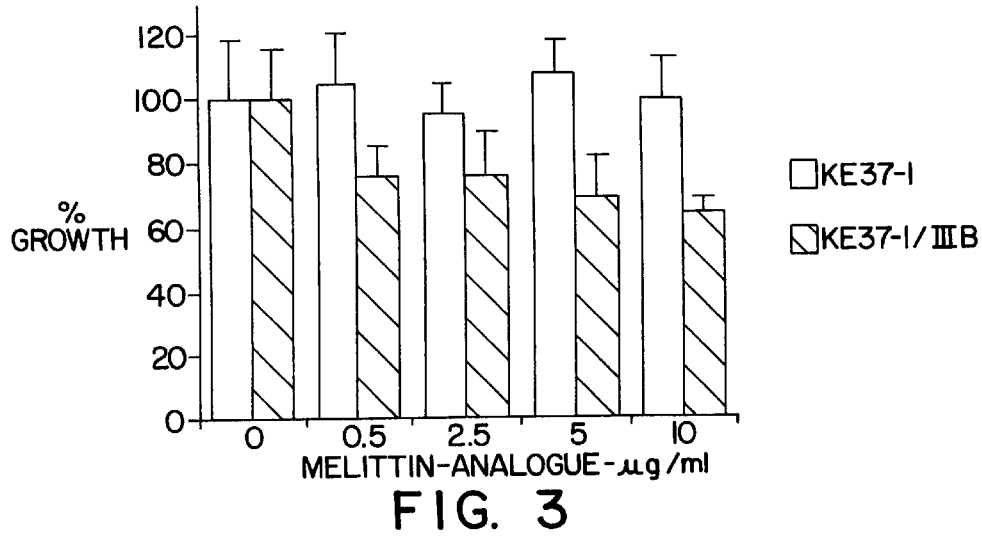
FIG. 3 is a graphic illustration which shows a comparison of the cell growth achieved for non-infected and HIV infected cells as a percentage of untreated controls and which are interdependent with the concentration of melittin analogues (Seq. ID NO:3–7 and 12).

The process of verifying the presence of HIV proteins was achieved through serological testing wherein antibodies to these proteins, that is primary antibodies and antibodies, directed to corresponding immunoglobulins, that is, secondary antibodies, and to which horse radish peroxidase is coupled, are employed. To visualize the antibody-antigen complex 3-aminoethylcarbazol was employed. This substance is not soluble in water. This procedure is better known as indirect immunoperoxidase coloration. This procedure is described at Mellert et al., "HTLV-III/LAV-Antikörpertest: Indirekte Immunperoxidasefärbung (HTLVIII/LAV antibody test: Indirect Immunoperoxidase staining," AIDS-FORSCHUNG (AIFO) February 1986 Heft 2, pp. 105–107. As best seen in FIGS. 1–4, it should be noted that melittin (Seq. ID NO:1) is toxic to both HIV infected cells as well as non-infected cells at concentrations above 5 μg per ml. In this regard, toxic studies relative to mice are provided hereinafter to further aid in analysis of the present test data. In addition to the foregoing, the specified melittin analogue (Seq. ID NO:3) as shown in FIG. 3 appears clearly less toxic than melittin. However, this same analogue develops a selective growth inhibiting effect with respect to HIV infected cells at higher dosages, that is, 10 μg per ml. Further, it should be noted that with a concentration of 5 μg per ml., at which melittin is toxic to both infected, as well as non-infected cells, the inventors have found that the growth of infected cells are reduced by almost 80% by utilizing melittin analogues (Seq. ID NO:3–7 and 12) after a period of approximately seven days while the growth of non-infected cells does not appear readily affected.

In addition to the foregoing, the test data as shown in FIGS. 1 through 4 illustrates that with a melittin (Seq. ID NO:1) concentration of 2.5 μg per ml., at which the level of growth of the cells appears not yet influenced, the ability of the cells to infect, as well as the activity of reverse transcriptase appear to revert substantially back to zero. This is shown most clearly by reference to FIG. 2.

Figure 4:
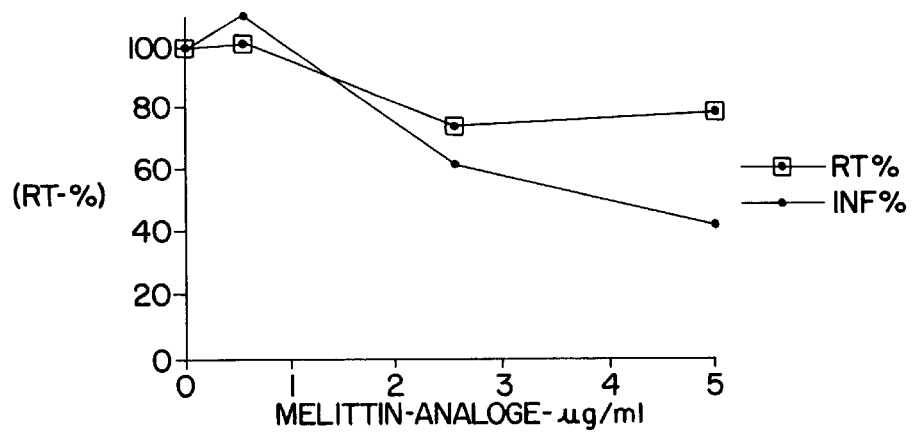
FIG. 4 is a graphic illustration of the activity of reverse transcriptase (RT%) as compared with a standardized number of cells and the infectivity (INF%) of the culture supernatant of HIV-infected T-lymphoma cells (KE37-1/111β) as a percentage of untreated controls and which are interdependent with the concentration of melittin analogues (Seq. ID NO:3–7 and 12).

The test data, as best seen by reference to FIG. 4, also shows that melittin analogues (Seq. ID NO:3–7 and 12) are also capable of lowering the activity of reverse transcriptase and the quantity of infectious virus cells in supernatant-treated HIV infected cells. This effect appears to occur in concentration ranges which are not yet toxic for non-infected cells, but clearly toxic for HIV-infected cells.

In summary, the test data shown in FIGS. 1–4 shows that melittin (Seq. ID NO:1) appears therapeutically useful for inhibiting viral replication at subtoxic concentrations by means of the inhibition of reverse transcriptase. Furthermore, melittin appears to inhibit the growth of HIV infected cells selectively which makes the elimination of the virus reservoir possible in mammals.

Additional tests were conducted to further supplement the test results shown in FIGS. 1 through 4. In these tests, which are illustrated most clearly by reference to FIGS. 6 through 34, respectively, the possible mechanism(s) by which melittin (Seq. ID NO:1) inhibits the growth of HIV infected cells was investigated. By way of introduction and referring more particularly to FIG. 5, energy minimization studies of the surface of HIV protein GP41 was conducted using the CHARMM algorithm on secondary structure predictions which were based on neural network computing principles. As should be understood, the application of a neural network program as used herein is to predict secondary protein structures from amino acid sequences.

Figure 5:
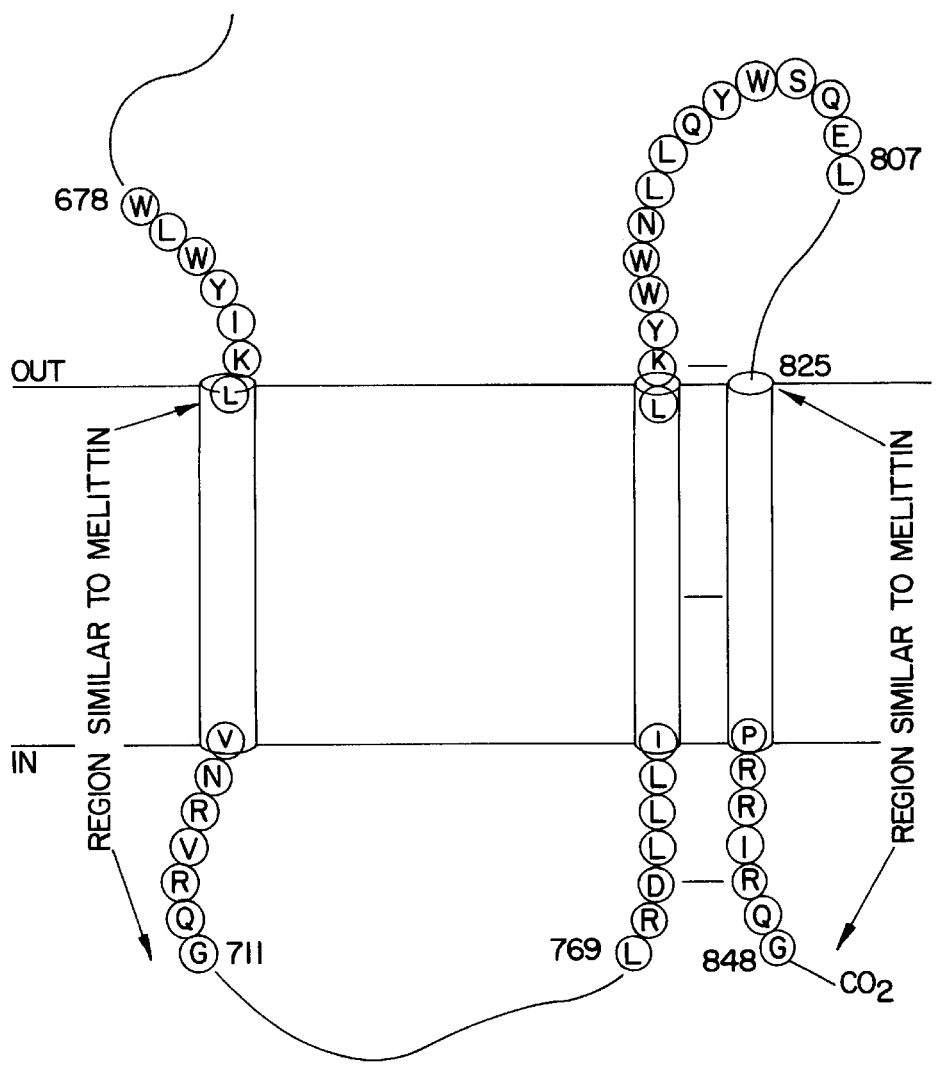
FIG. 5 is a graphic model of the carboxyterminal region of the GP41 molecule of the HIV virus.

This network has been trained to classify amino acid residues into three types of secondary structures: alphahelix, beta-sheet and random coil. By training it on a large set of proteins with known secondary structure, the neural network becomes able to make predictions about the secondary structure of proteins novel to the network, purely on the basis of their primary structure. An analysis of the secondary structure of the human immunodeficiency virus (HIV protein GP 41) by computer modeling based on neural network methods may be found at H. Andreassen et al., "Analysis of the Secondary Structure of the Human Immunodeficiency Virus (HIV) Proteins p17, gp120, and gp41 by Computer Modeling Based on Neutral Network Methods," *Journal of Acquired Immune Deficiency Syndromes*, v. 3 (1990), pp. 615–622. More particularly, the conclusions drawn from these studies shows that two transmembrane sections of the GP41 protein have a certain homology to the structure of melittin (Seq. ID NO:1). In this regard, this homology is quite noteworthy inasmuch as other analogues of melittin which are quite different from melittin appear to have the same HIV inhibiting effect. It appears, therefore, that several of the amino acids in melittin can be replaced without changing the activity of the molecule provided that the amphiphilicity is conserved, and polymerization of four melittin molecules by charge interaction is possible. The conclusions drawn from these tests, and which will be discussed in further detail hereinafter, is that melittin (Seq. ID NO:1) appears to interact with one of the major HIV proteins, glycoprotein GP41. This appears possible because of the similarity between the transmembrane regions of GP41 and melittin as shown in FIG. 5.

As should be understood, melittin (Seq. ID NO:1) is an amphiphilic peptide which is 26 amino acids long. In an aqueous solution of high ionic strength, melittin adopts a tetrameric configuration. At low ionic strengths, however melittin assumes a monomeric random coil. At physiologic ionic strengths the distribution between these two forms appears to be equal. Previous studies have shown that melittin (Seq. ID NO:1) appears to be able to adapt to the hydrophobic environment of a cell membrane by forming a monomeric alphahelix with the electrical charges distributed on one side of the helix and the uncharged side associated with the membrane. This research further indicates that the surface of the melittin polymer facing the surrounding lipid is thus uncharged. Further, another peculiar feature of the melittin molecule is that a kink of approximately 120° C. is introduced into the melittin helix by a proline (amino acid No. 14). A similar kink is found in the HIV GP41 melittin-like sequence which was discussed above.

Earlier studies have shown that melittin (Seq. ID NO:1) is known to have several effects. These effects are best described as a cell surface binding process and a polymerization process wherein alphahelices align to form a channel. Further, it has been shown that binding by the C-terminal, that is the 6 amino acids of the tail appears to be necessary for cell lysis. This fact is very important for understanding the experimental test data which will be described hereinafter. As should be understood the precise mechanism by which melittin (Seq. ID NO:1) forms a channel is not understood. It appears, however, that the melittin molecule binds to the phosphate anions with its basic C-terminus, thereby interacting with ten (10) phosphatidylcholine molecules. Once the melittin molecule is anchored, it appears to turn into the outer lipid layer of the membrane thereby disturbing the structure of the membrane. This activity is followed by formation of pores through the outer layer of the membrane thereby increasing ion permeability and a subsequent rupture of the membrane. The channels formed in the membrane appear to be stabilized by the melittin molecules. The formation of the channel also leads to lysis of the cells and which will hereinafter be referred to as the toxicity of melittin. This can be compared to the mechanism by which alphatoxin and complement are cytotoxic. Although these molecules may be capable of spanning the membrane thereby forming a pore with the same attendant results.

In addition to the effects involving the channel forming possibilities of amplilic peptides; an effect on phospholipase A2 has been described and which may also involve the amphiphilic interaction between two proteins. In this case, melittin (Seq. ID NO:1) may perhaps interact with the hydrophobic parts of the enzymatic protein phospholipase A2 or it may be due to melittin-phospholipid interactions. In addition to the foregoing, it is possible that the effects of melittin may also be intracellular. It is known, for example, that melittin stimulates endogenous phospholipase A2 in the anterior pituitary leading to growth hormone secretion.

A series of experiments and which are illustrated graphically in FIGS. 6 through 34, respectively, were designed to detect two extremes. In particular the tests were designed to detect the inhibition of viral release and/or the release of virus which has a reduced ability to infect other cells. This reduced ability to infect other cells is represented, for example, by glycosylation inhibitors, the direct effect on virus release is represented by acylation inhibitors, RT inhibitors and melittin (Seq. ID NO:1). The most important feature of this experimental design, however, is to detect the toxicity of melittin. The present experiments were carried out on both the astrocytoma cell line LC5-HIV (cloned infected cells) and T-lymphocytoma cell line KE37-1/IIIβ (cloned infected cells with HTLV-IIIβ). In both cases the results were essentially identical.

In the present series of experiments HIV release was tested by a fully automated laboratory robot system and which is manufactured by Beckman Instruments as the Biomek 1000. This system performed the following steps. First, chronically infected cells (cloned) are plated in microtiter plates and grown for a period of seven days. They are then challenged by melittin (Seq. ID NO:1) during this period either for the final day or throughout the period as shown in the figures. The number of living cells are quantified by MTT, that is by a metabolic (dehydrogenase) test. The MTT test is automatically performed. The toxic effect is detected at the time of the experiment and not in a separate control experiment. Furthermore, the supernatant, and which contains released virus cells from the period of time which elapsed from the last wash, and which may vary from 24 hours to 7 days, is collected from the culture, and an aliquot is saved for virus quantification by employing antigen or viral enzyme reverse transcriptase (RT). Furthermore, an aliquot is added to a culture of uninfected cells in microtiter plates for subsequent measurement of the ability of the virus cells to reinfect these uninfected cells. In this regard, the number of infected cells is automatically quantified by an immunoperoxidase staining technique. The test results, as shown, are expressed in terms of toxicity of the melittin (MTT test); the release of HIV from the primary culture (RT test); and the ability of the released virus to infect previously uninfected cells.

Figure 6:
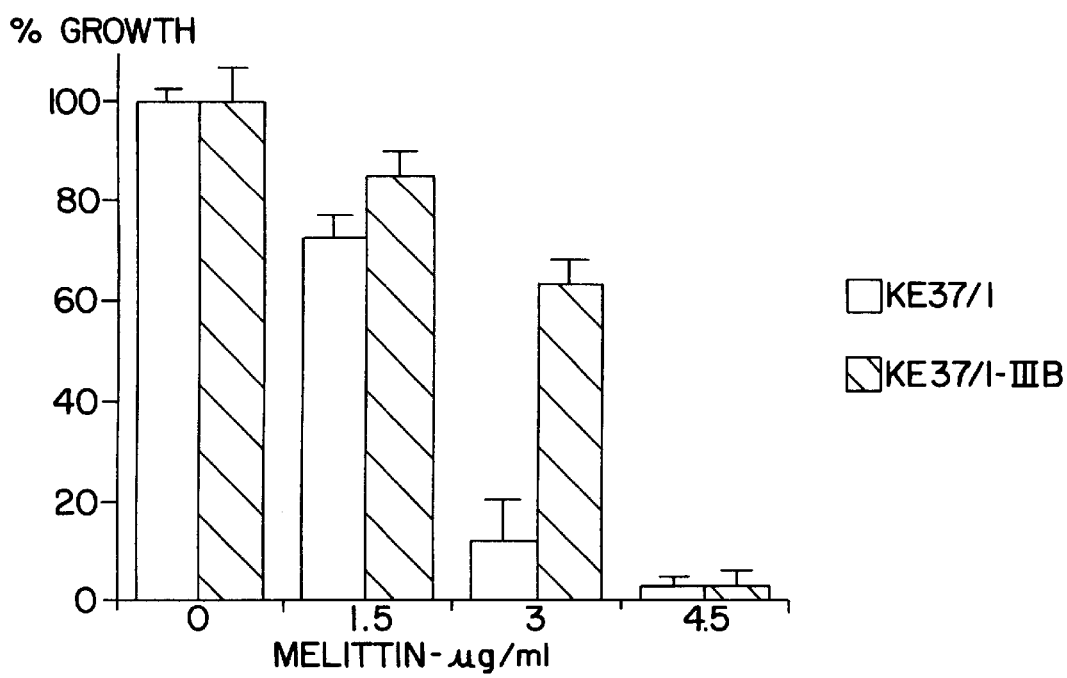
FIG. 6 is a graphic illustration which shows a comparison of cell growth achieved for HIV infected, and non-infected cells as a percentage of untreated controls and which are interdependent with the concentration of melittin (Seq. ID NO:1).
Figure 7:
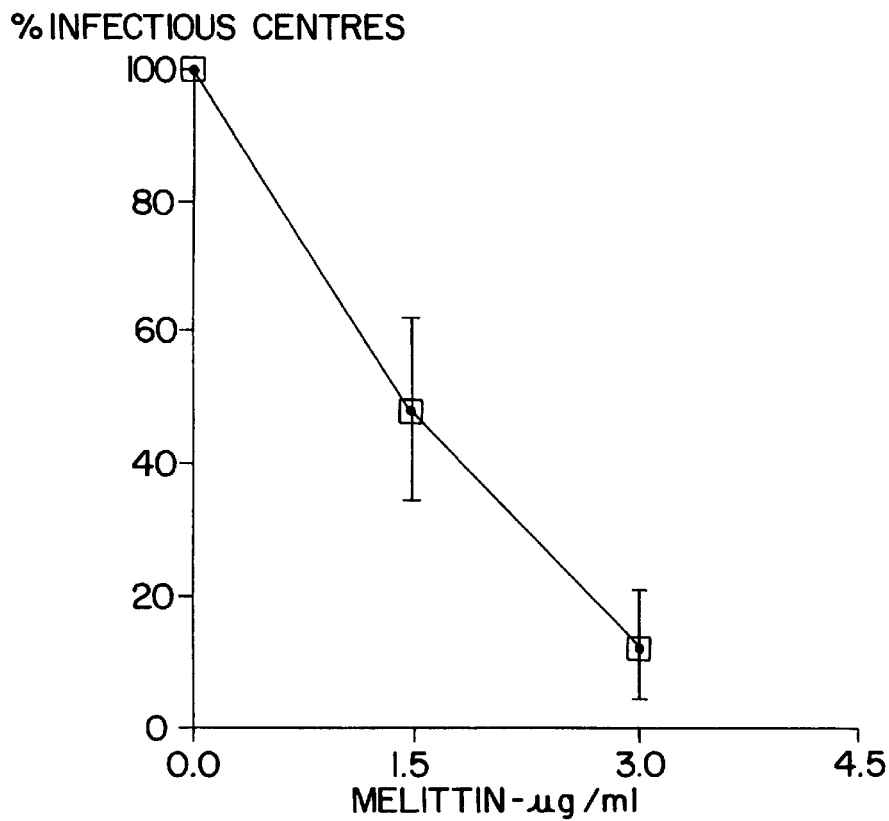
FIG. 7 is a graphic illustration which shows the percentage of infectious cells as a function of the concentration of melittin (Seq. ID NO:1).
Figure 8:
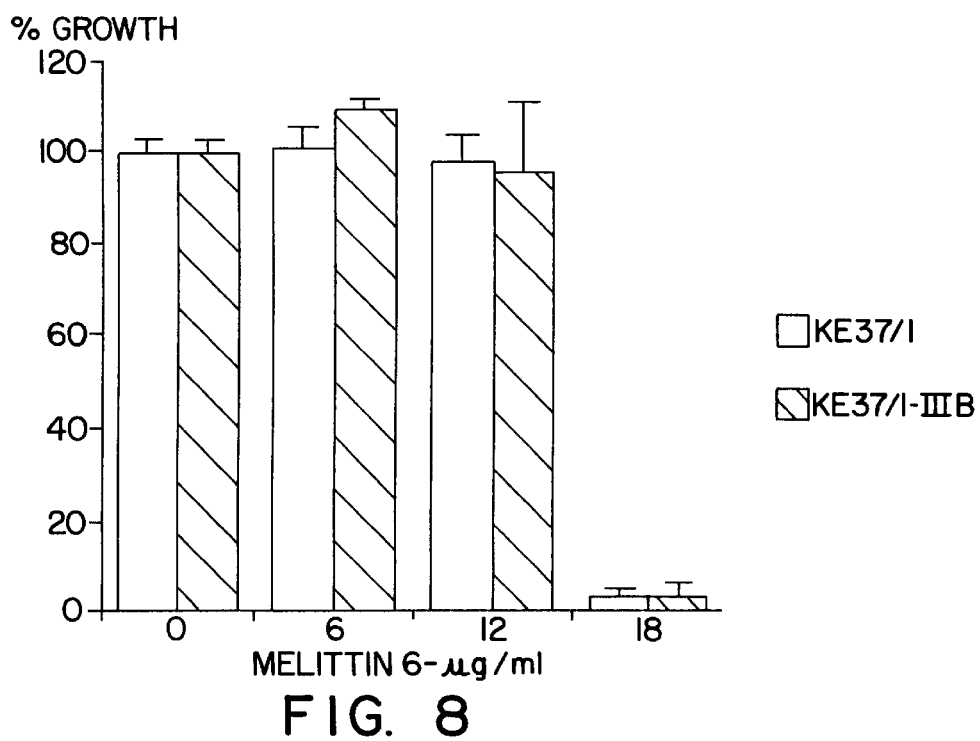
FIG. 8 is a graphic illustration which shows a comparison of cell growth achieved with HIV infected and non-infected infected cells as a percentage of untreated controls and which are interdependent with the concentration of melittin (Seq. ID NO:5) 6.
Figure 9:
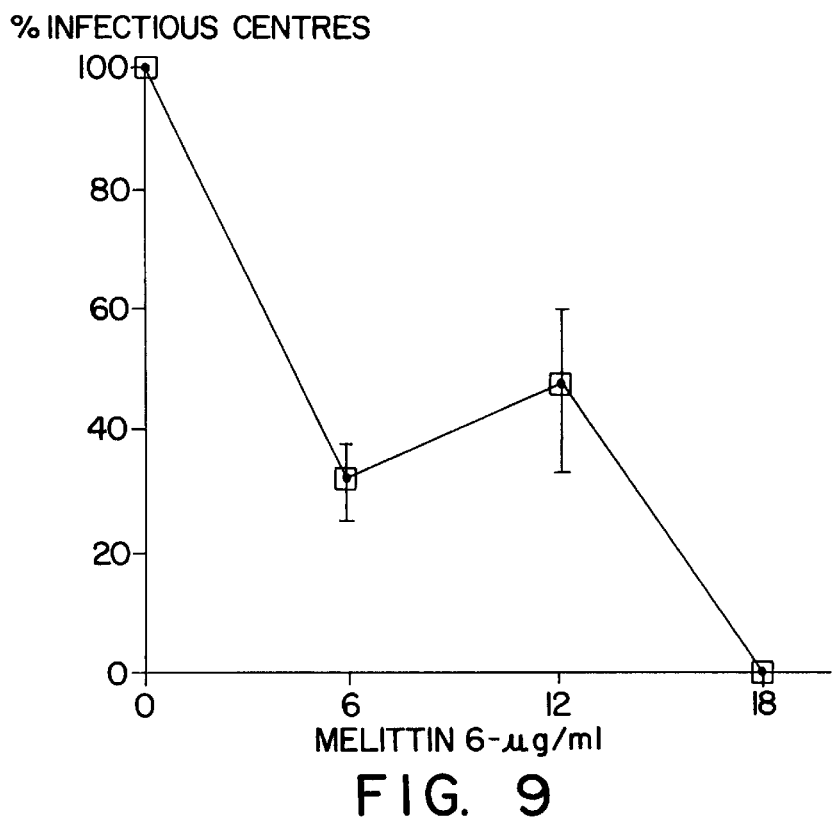
FIG. 9 is a graphic illustration which shows the percentage of infectious cells as a function of the concentration of melittin (Seq. ID NO:3) 6.
Figure 10:
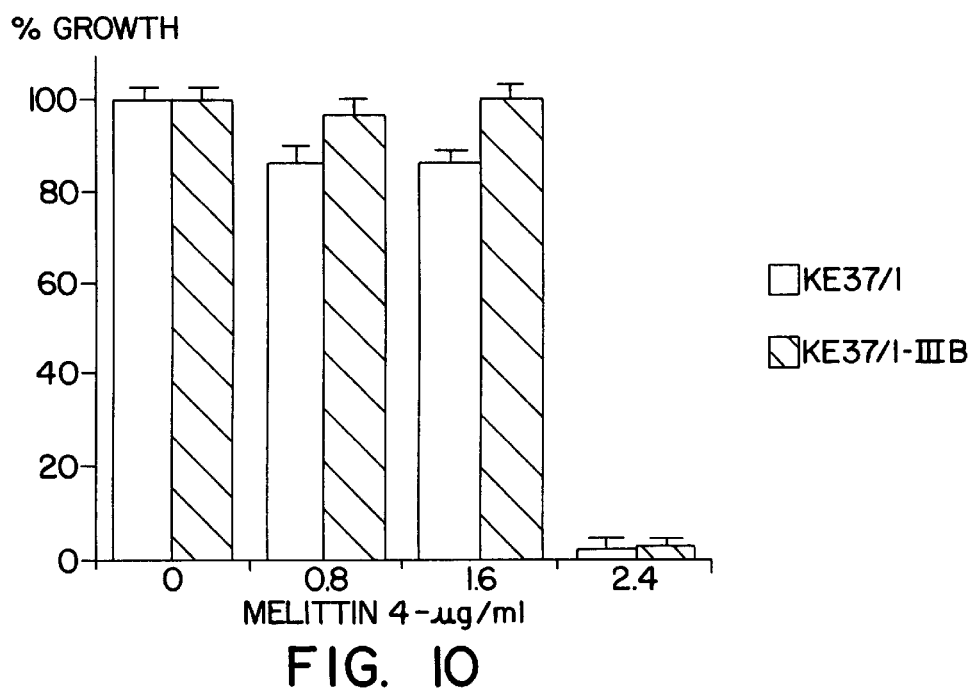
FIG. 10 is a graphic illustration which shows the percentage of cell growth achieved for HIV infected and non-infected cells as a percentage of untreated controls and which are interdependent with the concentration of melittin 4 (Seq. ID NO:4).
Figure 11:
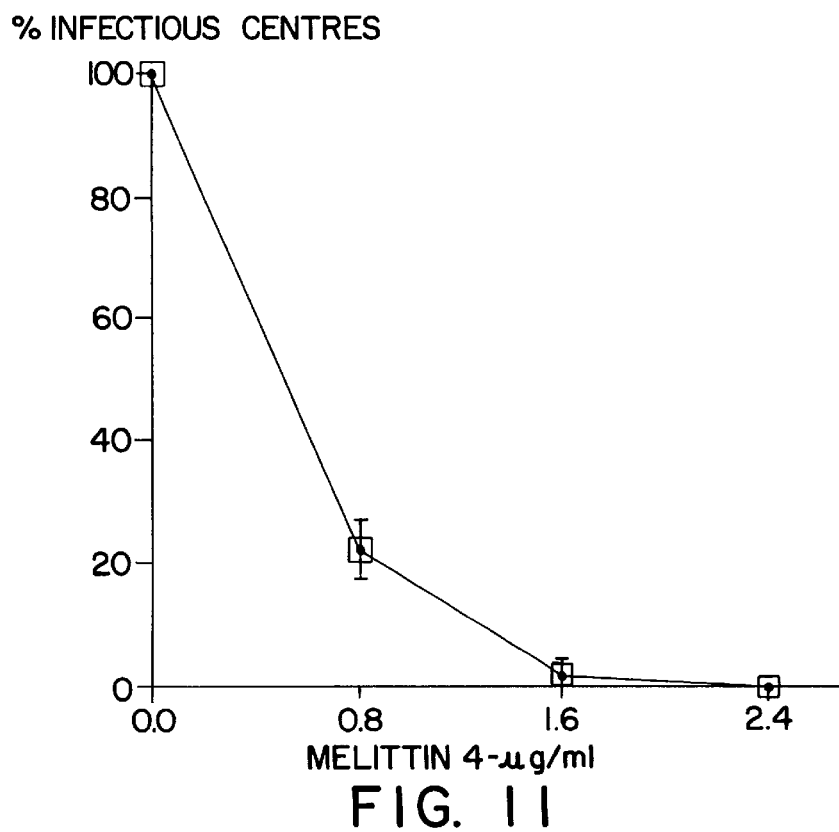
FIG. 11 is a graphic illustration which shows the percentage of infectious cells as function of the concentration of melittin 4 (Seq. ID NO:4).
Figure 12:
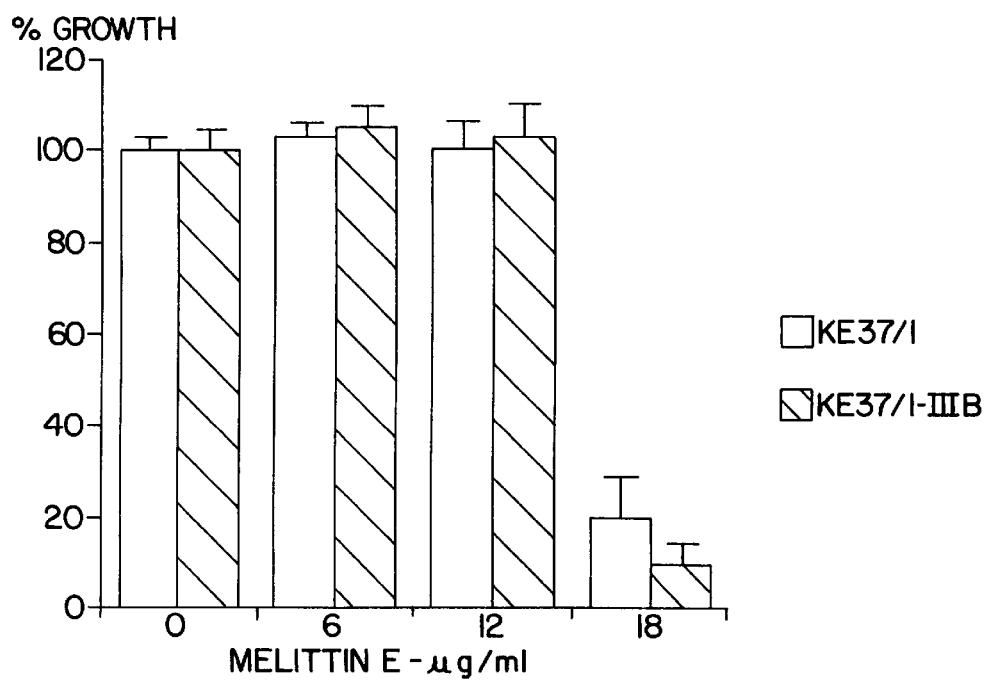
FIG. 12 is a graphic illustration which shows the percentage of cell growth achieved for HIV infected and non-infected infected cells as a percentage of untreated controls and which are interdependent with the concentration of melittin E (Seq. ID NO:5).
Figure 13:
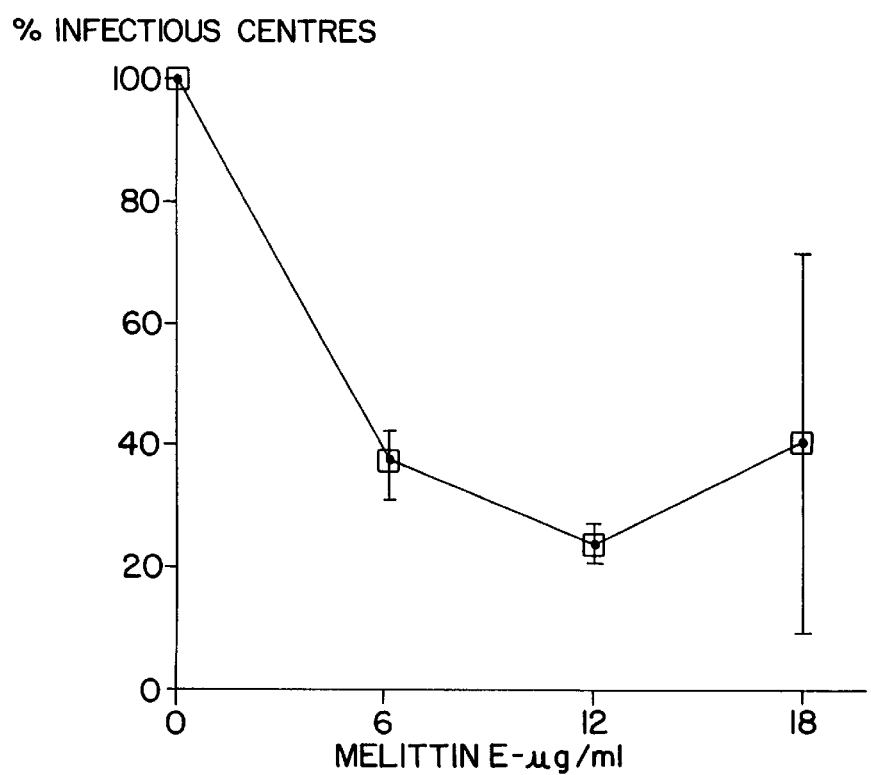
FIG. 13 is a graphic illustration which shows the percentage of infectious cells as a function of the concentration of melittin E (Seq. ID NO:5).
Figure 14:
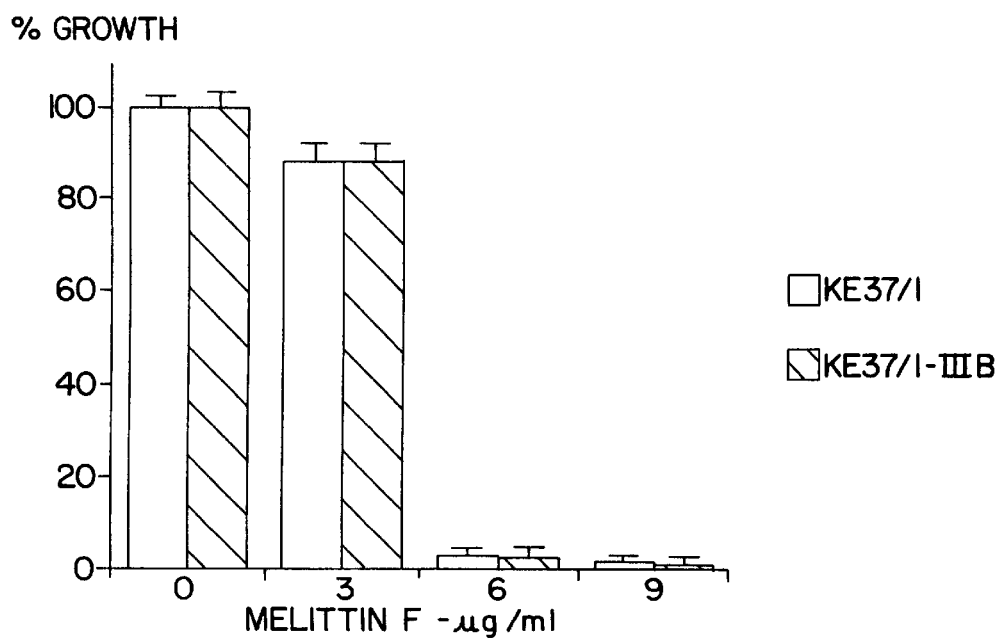
FIG. 14 is a graphic illustration of the percentage of cell growth achieved for HIV infected and non-infected cells as a percentage of untreated controls and which are interdependent with the concentration of melittin E (Seq. ID NO:6).
Figure 15:
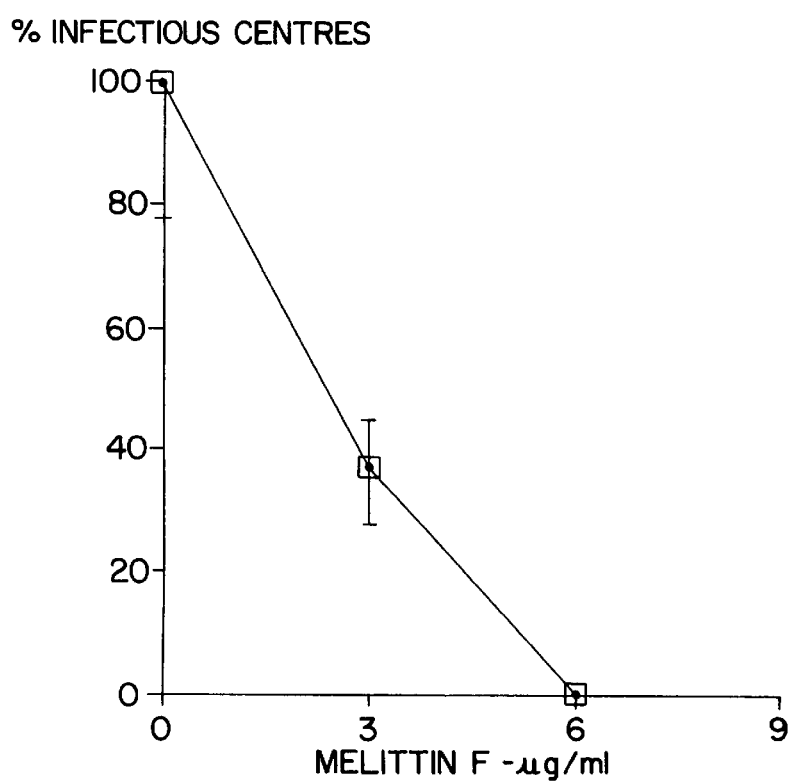
FIG. 15 is a graphic illustration which shows the percentage of infectious cells as a function of the concentration of melittin F (Seq. ID NO:6).
Figure 16:
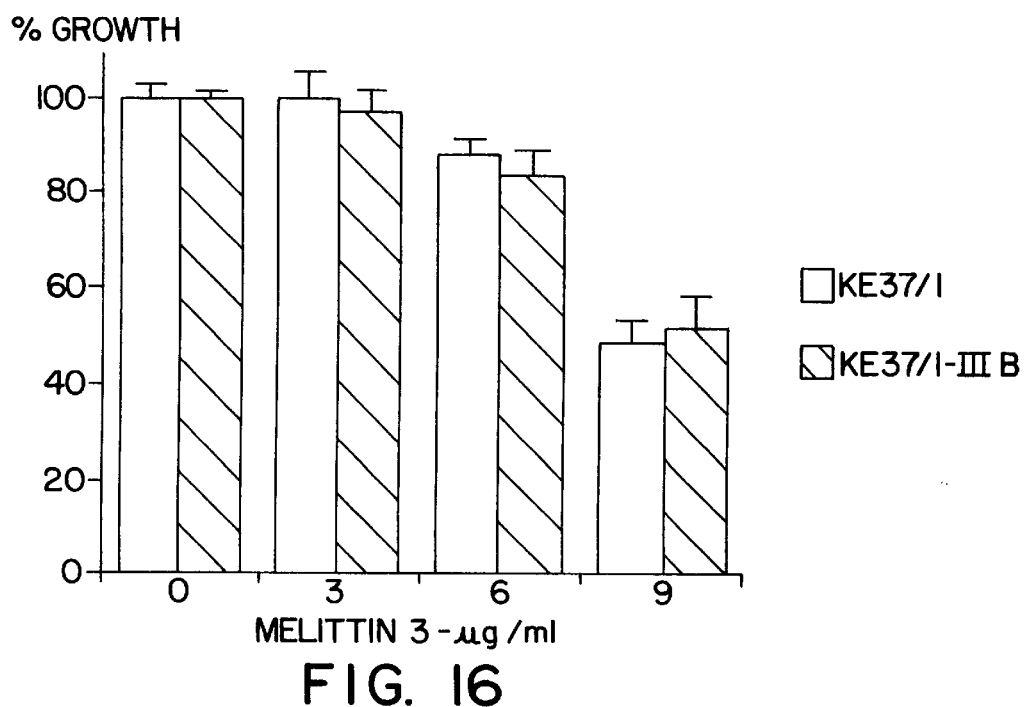
FIG. 16 is a graphic illustration which shows the percentage of cell growth achieved for HIV infected, and non-infected infected cells as a percentage of untreated controls and which are interdependent with the concentration of melittin 3 (Seq. ID NO:12).
Figure 17:
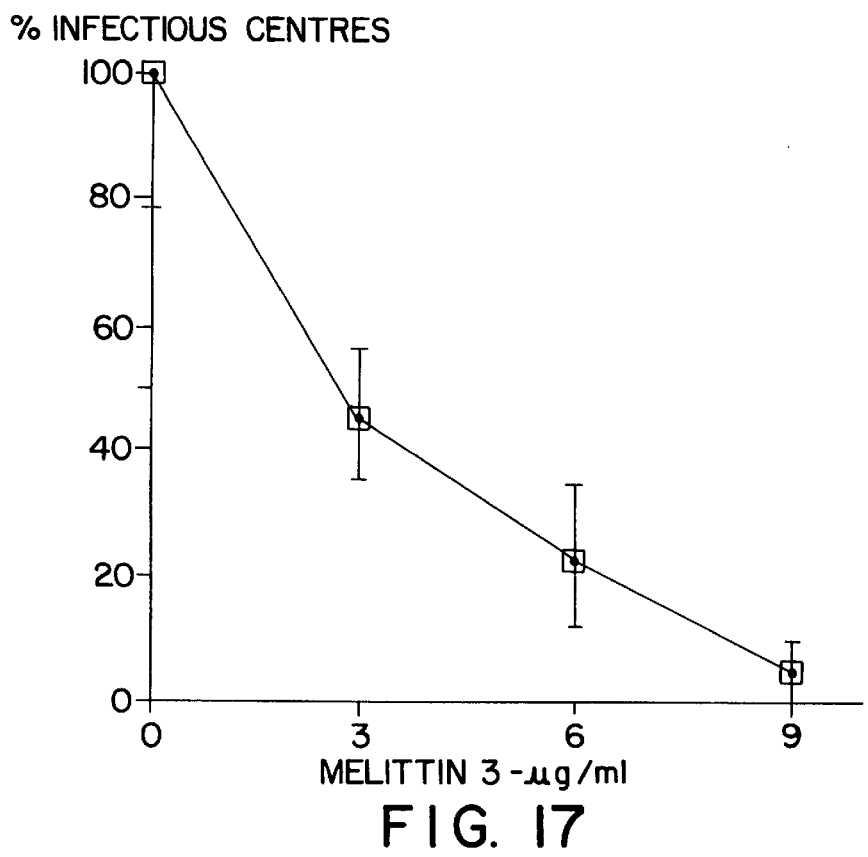
FIG. 17 is a graphic illustration which shows the percentage of infectious cells as a function of the concentration of melittin 3 (Seq. ID NO:12).
Figure 18:
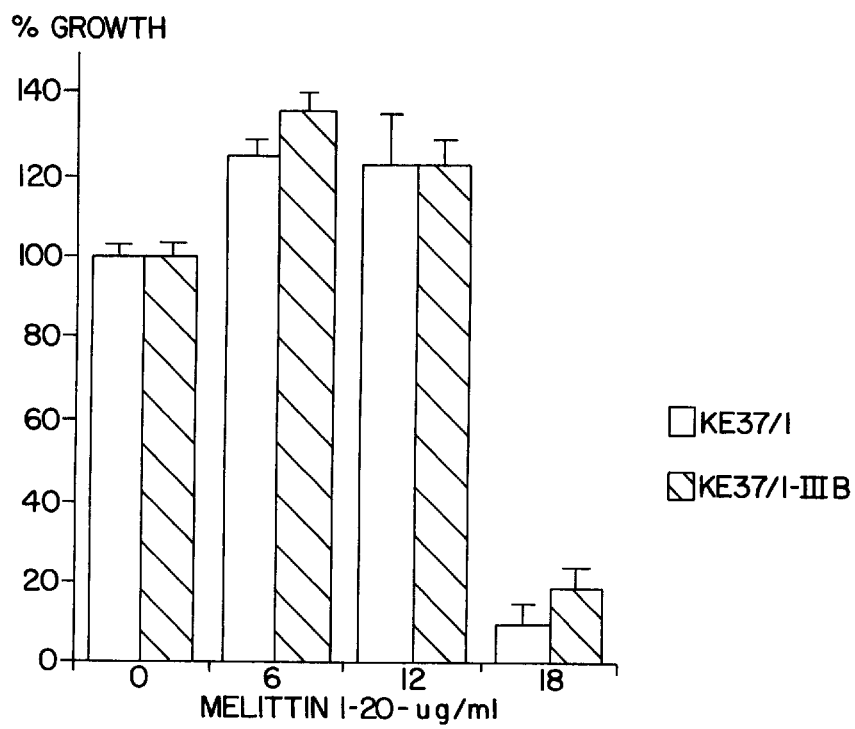
FIG. 18 is a graphic illustration which shows the percentage of cell growth achieved for HIV infected and non-infected cells as a percentage of untreated controls and which are interdependent with the concentration of melittin 1–20 (Seq. ID NO:7).
Figure 19:
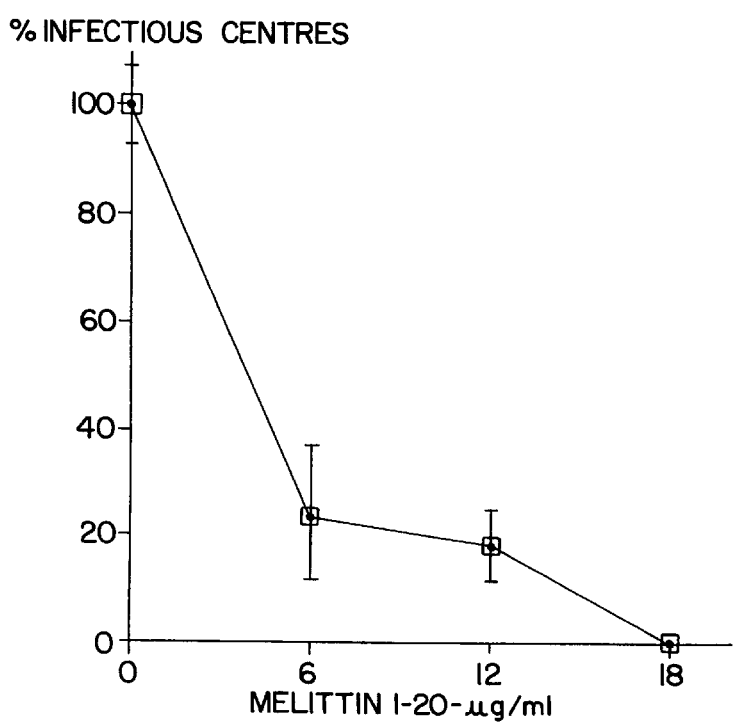
FIG. 19 is a graphic illustration which shows the percentage of infectious cells as a function of the concentration of melittin 1–20 (Seq. ID NO:7).

As best seen by reference to FIGS. 6 and 7 the overall effect of melittin (Seq. ID NO:1) on HIV infected cells appears to be the inhibition of viral cell release from infected cells (FIG. 6), but in its natural form it appears to not selectively affect the infected cells (FIG. 7). This relationship is also shown with respect to melittin 6 (Seq. ID NO:3) (FIGS. 8 and 9); melittin 4 (Seq. ID NO:4) (FIGS. 10 and 11); melittin E (Seq. ID NO:5) (FIGS. 12 and 13); melittin F (Seq. ID NO:6) (FIGS. 14 and 15); melittin 3 (Seq. ID NO:12) (FIGS. 16 and 17); and melittin 1–20 (Seq. ID NO:7) (FIGS. 18 and 19); respectively. The information derived from this test data is noteworthy inasmuch as the membranolytic effect of melittin appears dependent on the surface binding of the melittin to cells via its C-terminal. As earlier discussed, this binding process also appears dependent on positive charges due to the C-terminal sequence which includes an amino acid sequence of Lys-Arg-Lys-Arg-Gln-Gln-Amide. To determine whether the effect of melittin (Seq. ID NO:1) was based on the known mechanism of channel formation or due to an unknown process the inventors tested (1–20)-6-(Gly)-Amide. It was reasoned that due to its lack of charges this form of melittin should act in a fashion consistent with its amphiphilic properties and not be dependent on the specific interaction with the cell surface. Contrary to the inventors' hypothesis, however, and as best seen by reference to FIGS. 18 and 19, it appeared clear that melittin analogues that do not specifically bind to the cell surface and are therefore much less toxic appear to inhibit viral cell release and also selectively kill HIV infected cells. This experimental data tends to indicate that the toxic, cytolytic effective of melittin may conceivably mask the selective killing of infected cells. This would be expected if the lytic properties of melittin were not involved in its anti-HIV effects. It is thus a novel and hitherto unexplored aspect of melittin action.

The test results further clearly shows that natural melittin (Seq. ID NO:1) was able to lyse HIV-infected LC5 cells. The test data showed, for example, that the nature of this action appeared to be related to the critical concentration phenomenon of same. More particularly, and when the critical concentration was reached (10 µg per ml.) all cells, that is, infected and non-infected, were killed. This effect happened at concentrations ten times higher than the effect on HIV release. Melittin COOH was tested and appeared to be less efficient than the melittin amid. In addition to the foregoing, two melittin analogues were tested, which lacked the binding tail of positively charged amino acids in positions 21 through 26. These melittin analogues both had the same pronounced effect on HIV infected cells, that is these infected cells were selectively killed. For example, and at 10 µg per ml., half of the infected cells were killed, whereas the uninfected cells were essentially unaffected. Moreover, no lysis of the cells that could be described as toxicity of melittin due to lysis at a critical concentration was observed in the concentrations used. The effect of melittin analogues showed a steady decline in the survival of infected cells by increasing the concentrations of the analogues. This effect of the melittin analogues is not easily explained. That is, infected cells are apparently viable to the same extent as uninfected cells and therefore would not be expected to die at a higher rate than uninfected cells if HIV release was inhibited. Moreover, the effect of melittin (Seq. ID NO:1) as an anti-viral substance acting through its amphiphilic structure was further substantiated by the effects of melittin (1–20) FIGS. 18 and 19, respectively. It should be understood, in this regard, that melittin 1–20 (Seq. ID NO:7) lacks the cell binding part of the molecule. This analogue, however, notwithstanding inhibited HIV release as did the natural melittin and melittin (1–20)-6-(Gly)-Amide. Moreover this same melittin also inhibited the growth of infected cells as did the melittin without the positively charged C-terminal, that is melittin (1–20-6-(Gly)-Amide. Therefore, the antiviral effect of melittin appears to be independent of the known cell lytic mechanisms of melittin but rather appeared dependent on the amphiphilic and membrane chaotropic effects of melittin. The selective killing of infected cells may therefore be a function of the inhibition of HIV release, although this is at the present time speculative and the effect may be due to a hitherto undiscovered effect of melittin.

Figure 20:
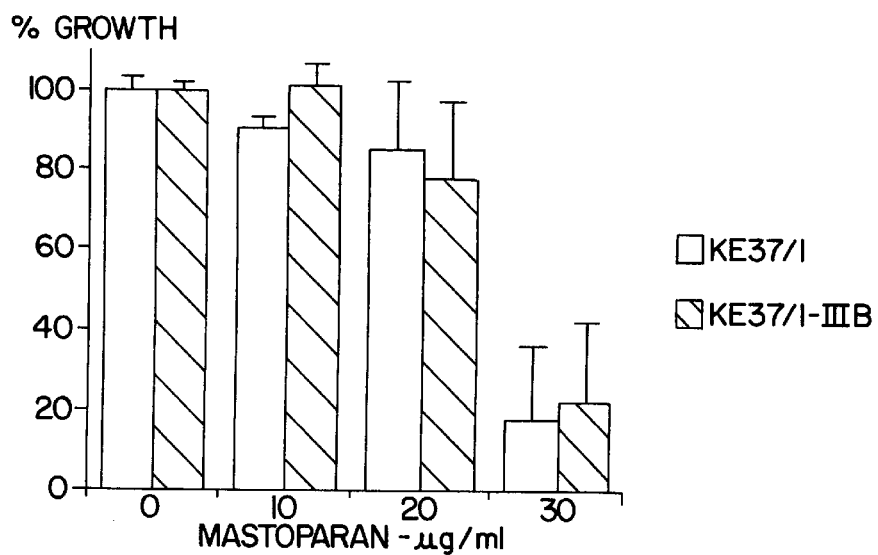
FIG. 20 is a graphic illustration which shows the percentage of cell growth achieved for HIV infected and non-infected infected cells as a percentage of untreated controls and which are interdependent with the concentration of mastoparan.
Figure 21:
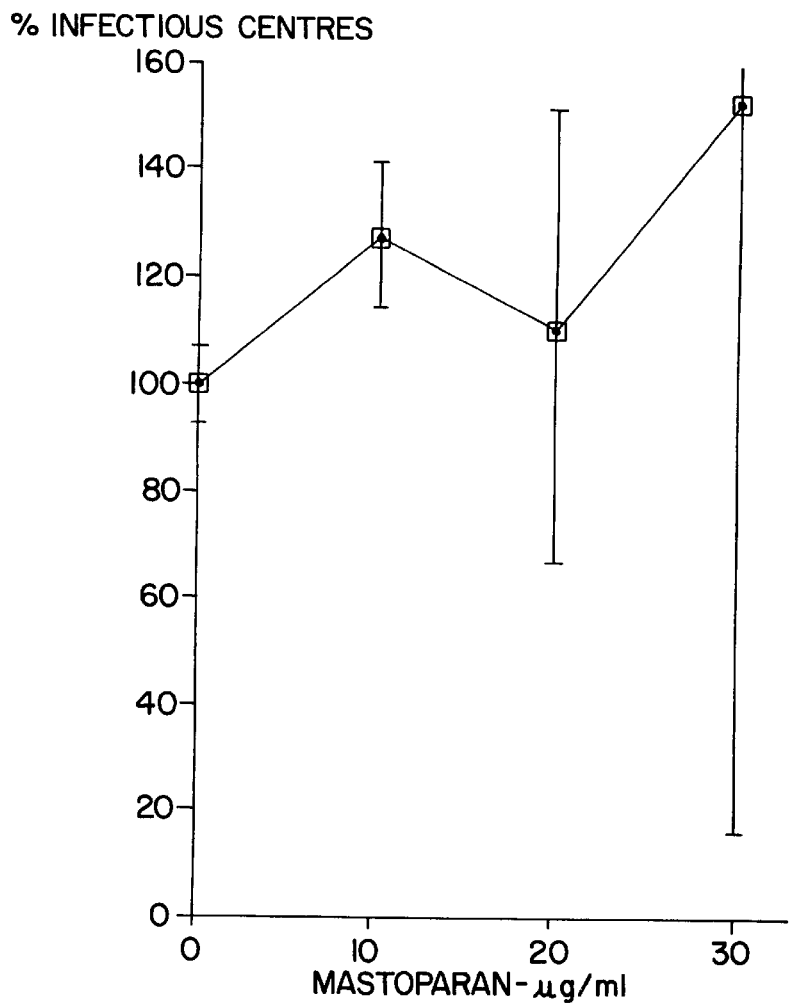
FIG. 21 is a graphic illustration which shows the percentage of infectious cells as a function of the concentration of mastoparan.
Figure 22:
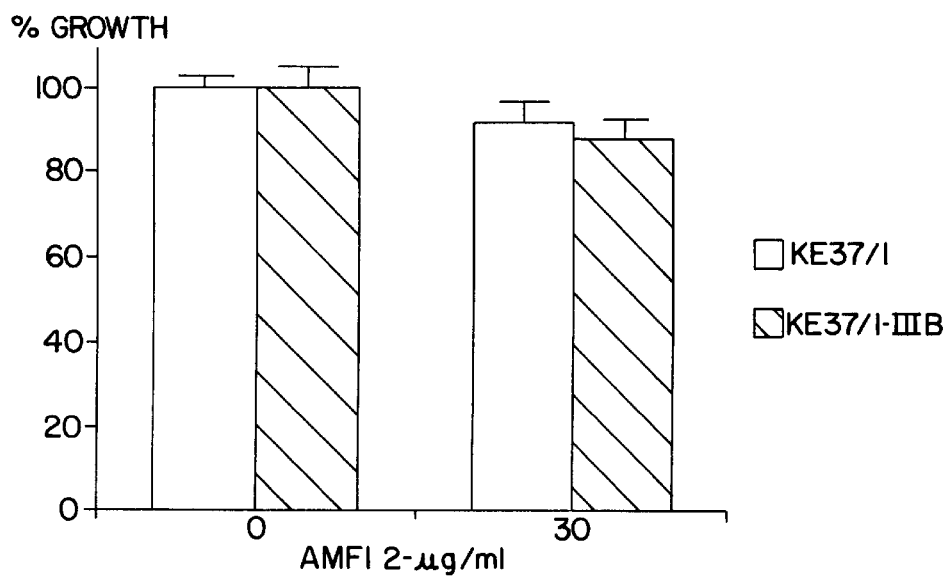
FIG. 22 is a graphic illustration which shows the percentage of cell growth achieved for HIV infected and non-infected cells as a percentage of untreated controls and which are compared with the concentration with AMFI 2. The percentage of cell growth for HIV infected and non-infected cells as a percentage of untreated controls and which are compared with the concentration of AMFI 1 is identical to the results depicted in FIG. 22 (Seq. ID NO:8).
Figure 23:
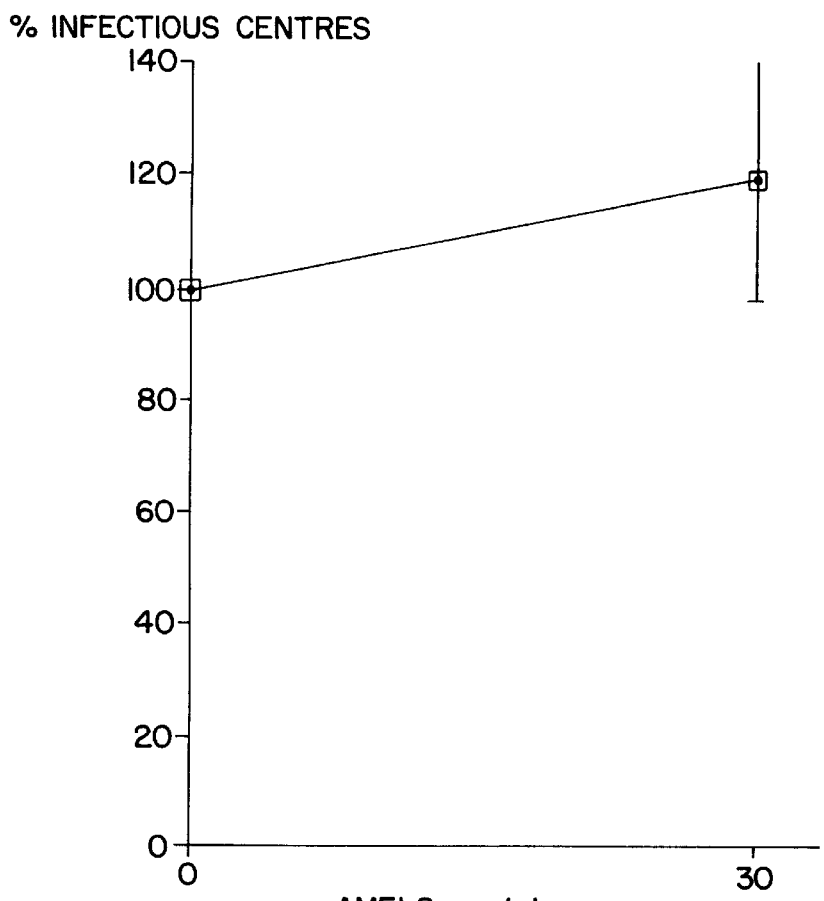
FIG. 23 is a graphic illustration which shows the percentage of infectious cells as a function of the concentration of AMFI 2. The percentage of infectious cells as a function of the concentration of AMFI 1 is identical to the results depicted in FIG. 23 (Seq. ID NO:8).
Figure 24:
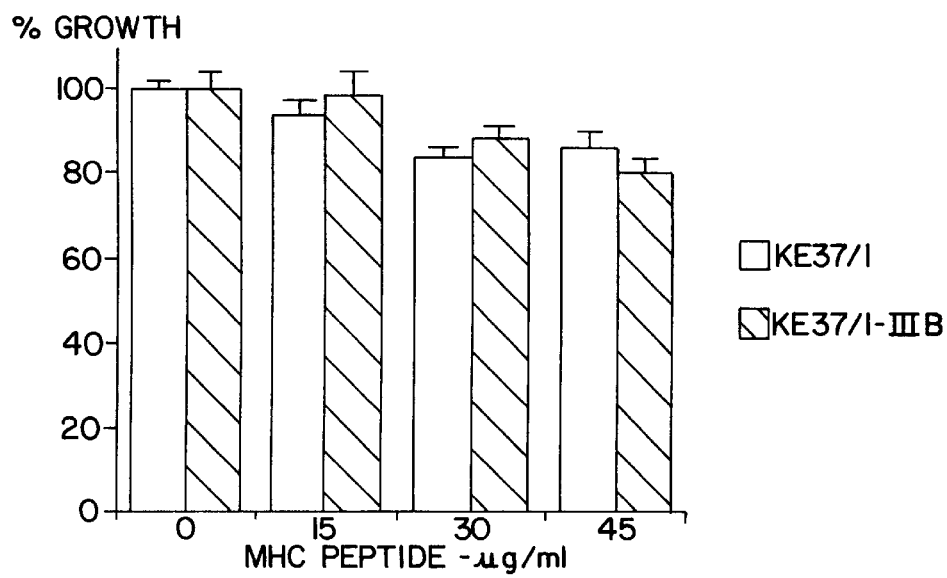
FIG. 24 is a graphic illustration which shows the percentage achieved for cell growth of HIV infected and non-infected infected cells as a percentage of untreated controls and which are compared with the concentration of MHC peptide (Seq. ID NO:10).
Figure 25:
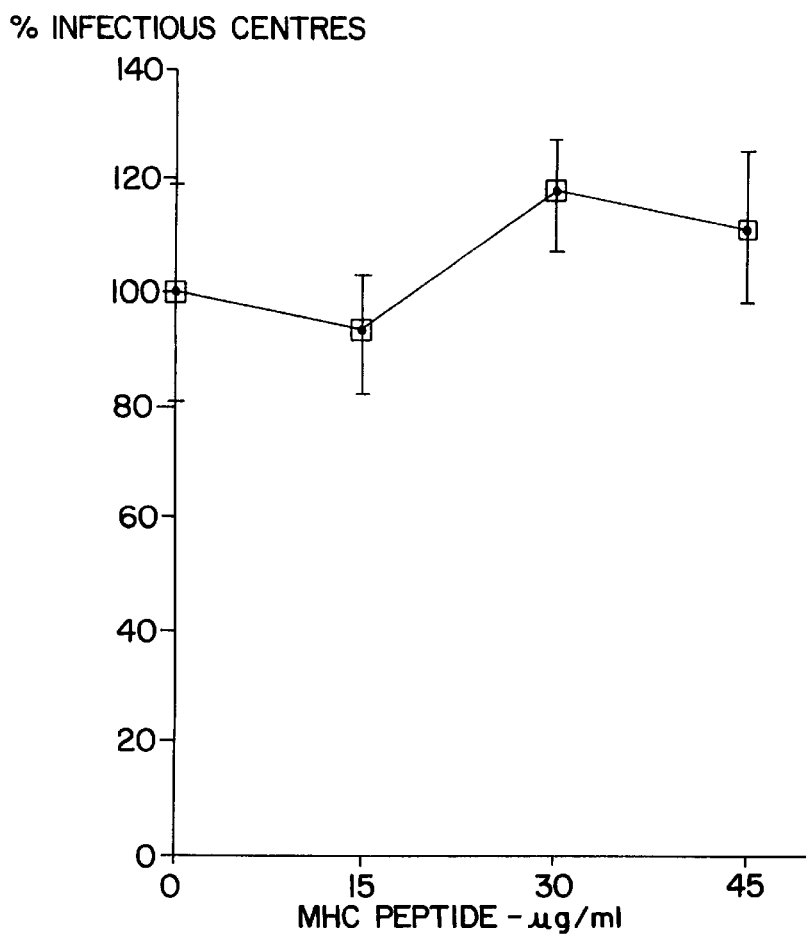
FIG. 25 is a graphic illustration which shows the percentage of infectious cells as a function of the concentration of MHC peptide (Seq. ID NO:10).
Figure 26:
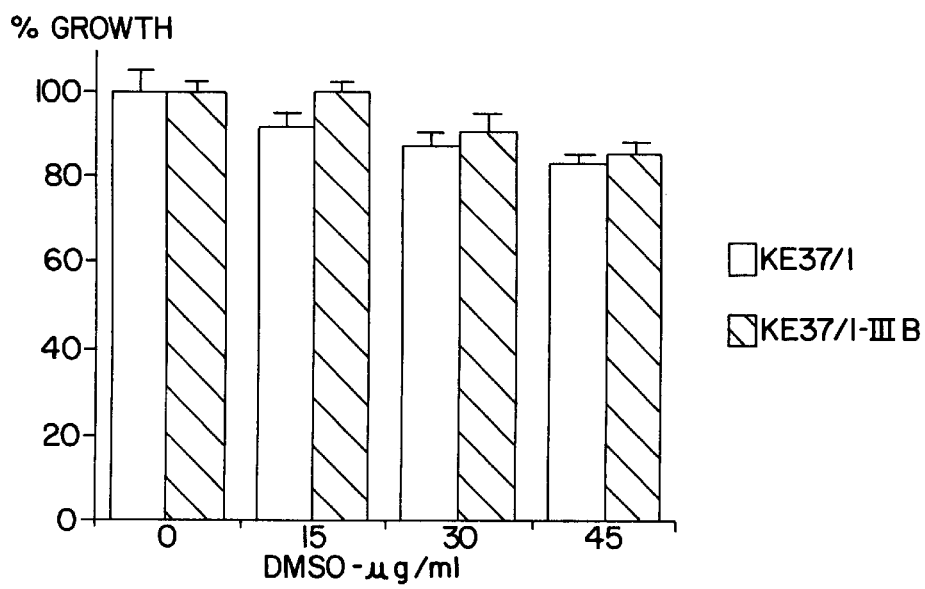
FIG. 26 is a graphic illustration which shows the percentage achieved for cell growth of HIV infected and non-infected infected cells as a percentage of untreated controls and which are compared to the concentration of DMSO (solvent control).
Figure 27:
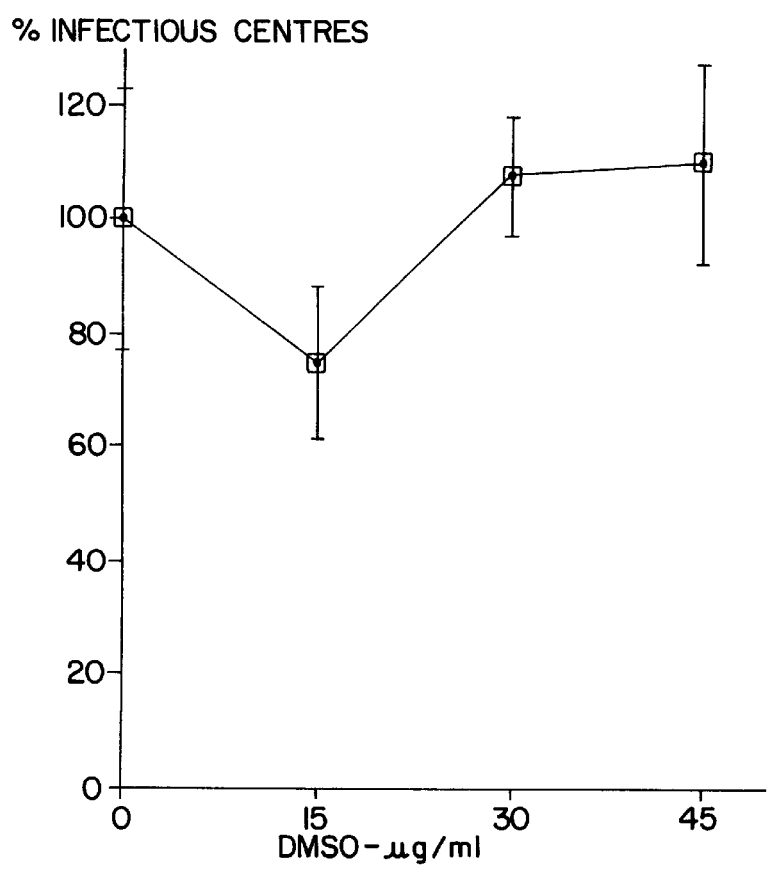
FIG. 27 is a graphic illustration which shows the percentage of infectious cells as a function of the concentration of DMSO (solvent control).
Figure 28:
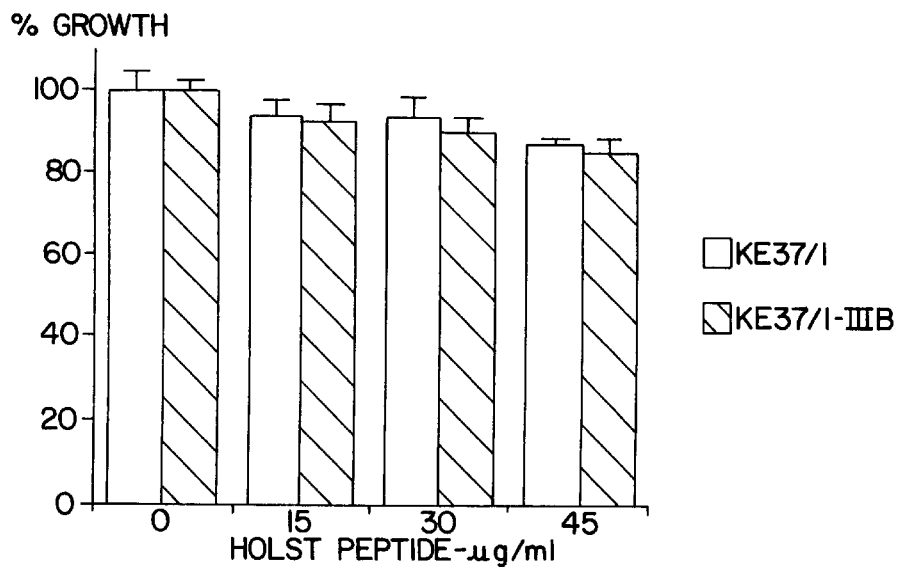
FIG. 28 is a graphic illustration which shows the percentage of cell growth achieved for HIV infected and non-infected cells as a percentage of untreated controls and which are compared with the concentration of the HOLST peptide (negative control) (Seq. ID NO:11).
Figure 29:
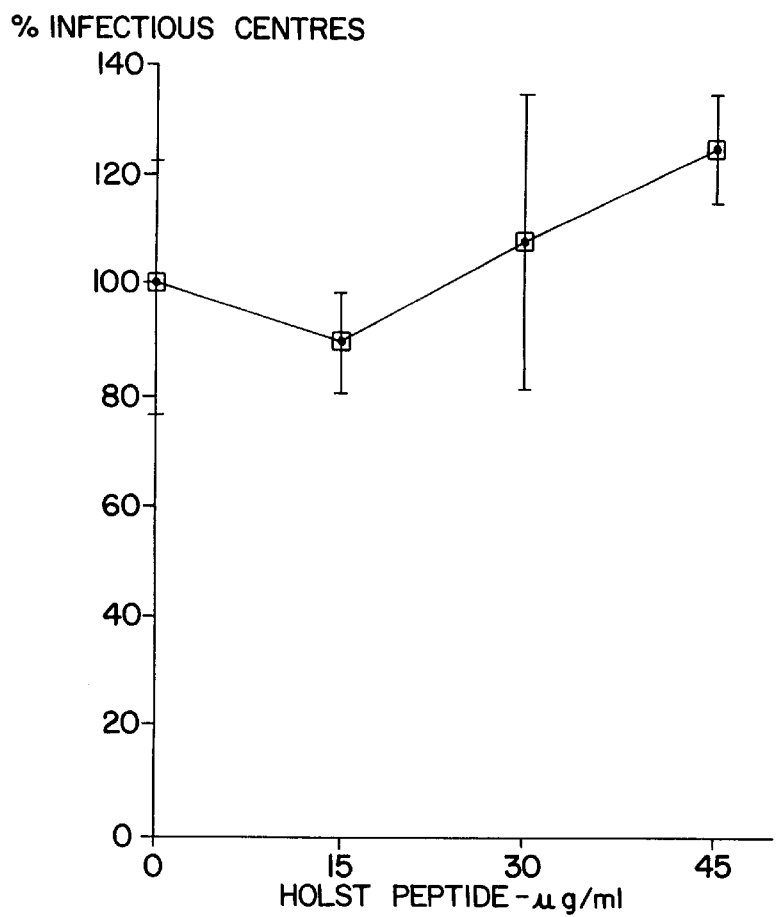
FIG. 29 is a graphic illustration which shows the percentage of infectious cells as a function of the concentration of the HOLST peptide (Seq. ID NO:11).

The effects of the toxin mastoparan and which are shown in FIGS. 20 and 21 were also explored. This is also an amphiphilic peptide but it is considerably shorter and contains only 14 amino acid residues. Therefore, it is only capable of spanning the membrane in a polymerized form. The results are summarized in FIGS. 20 and 21. It is important to note that peptides with similar structure, that is, MHC (Seq. ID NO:10), (MAJOR histocompatibility complex sequence), and GP41 analogues, as well as mastoparan do not have any readily apparent effects. Further, a control peptide but which has no apparent structural similarity to melittin is also without effect.

Figure 30:
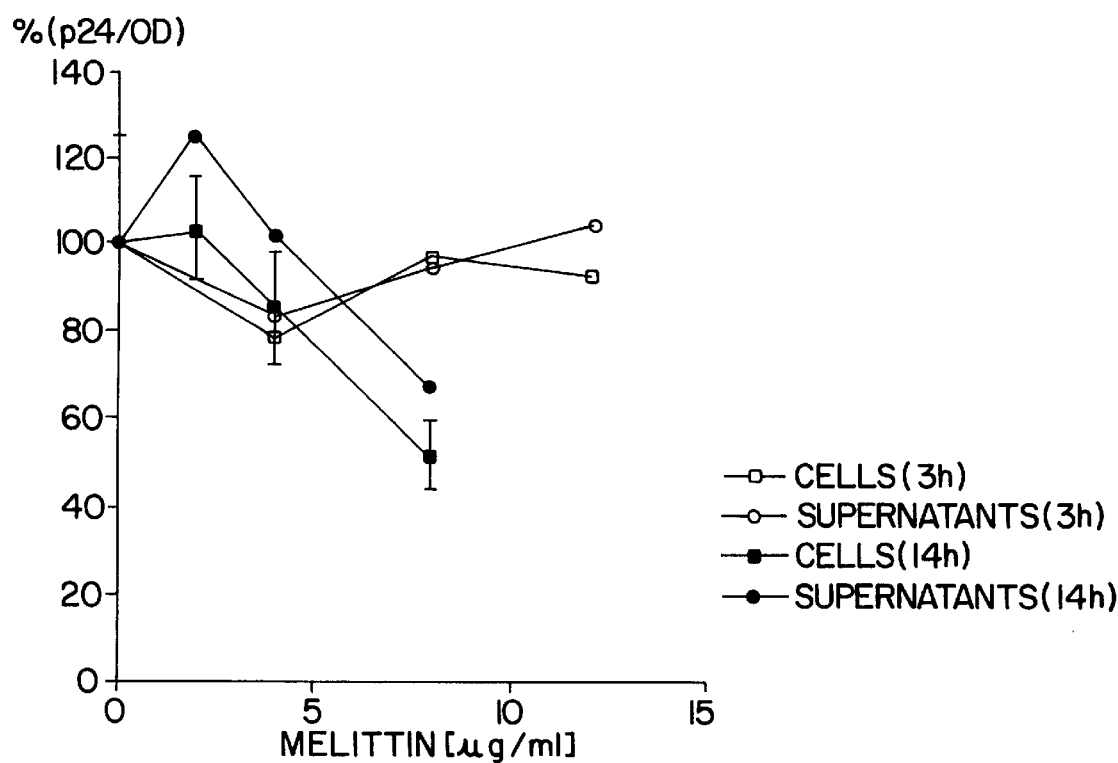
FIG. 30 is a graphic illustration which shows the percentage of P24 production as compared with the concentration of melittin (Seq. ID NO:1) at various time intervals.
Figure 31:
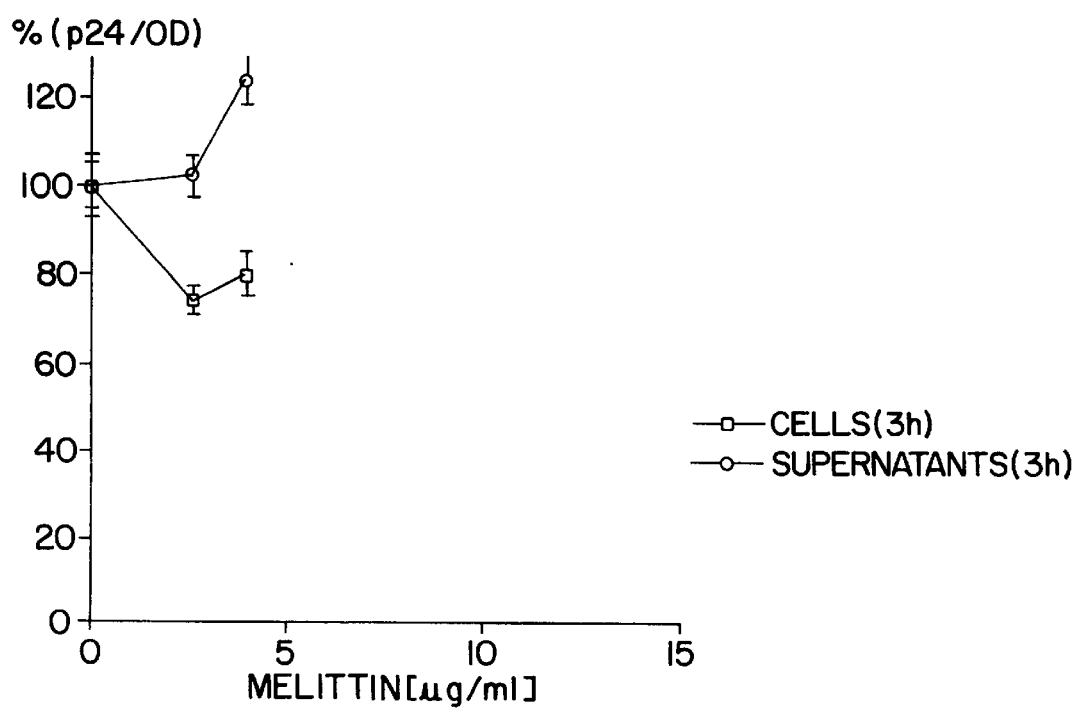
FIG. 31 is a graphic illustration which shows the percentage of P24 production in cells and supernatant in comparison to the concentration of melittin (Seq. ID NO:1) at a period of three hours.
Figure 32:
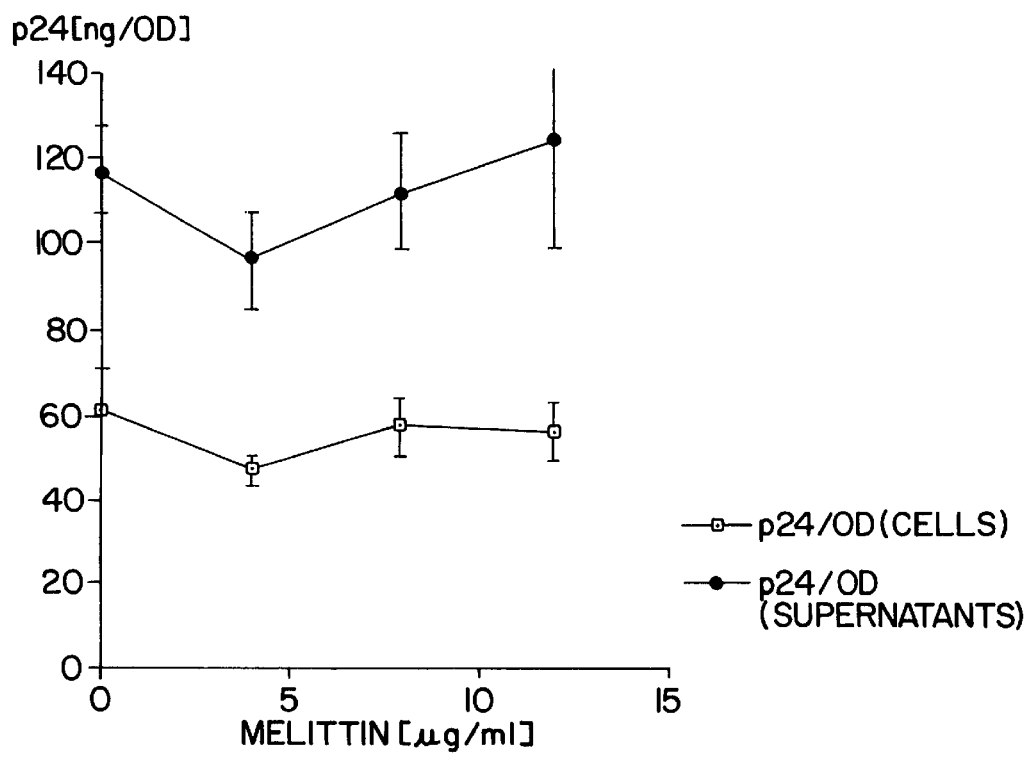
FIGS. 32 and 33 are graphic illustrations which shows the concentration of P24 in cells and supernatants following three hours and fourteen hours of incubation in the presence of melittin (Seq. ID NO:1) respectively.
Figure 33:
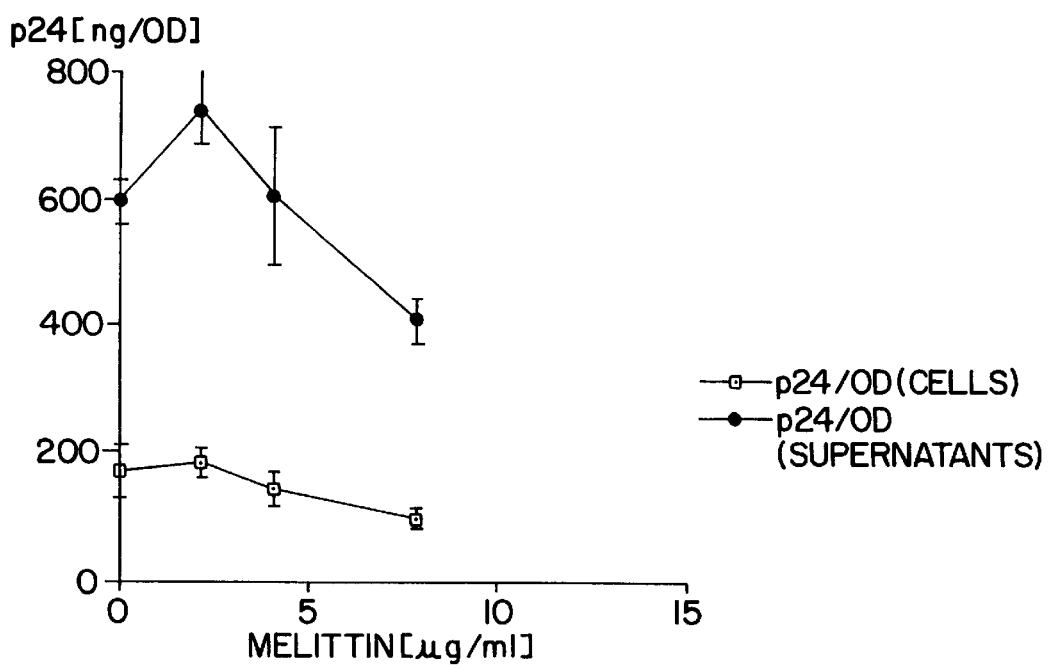
Figure 34:
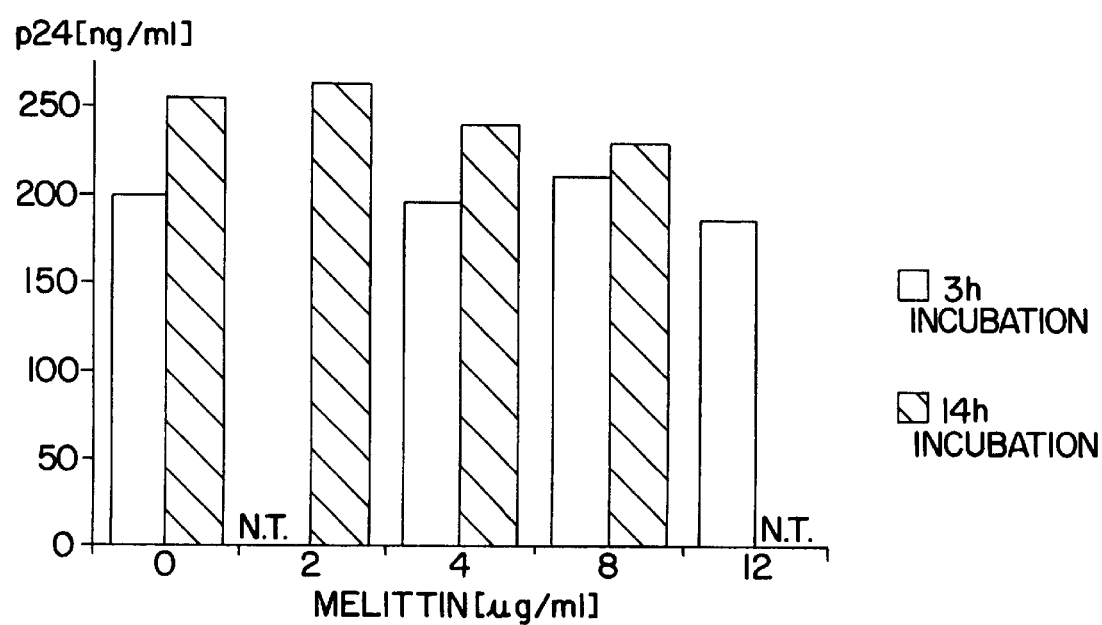
FIG. 34 is a graphic illustration which shows the influence of melittin (Seq. ID NO:1) on the P24 determination in cell free HIV supernatants at three and fourteen hours, respectively, after incubation with various concentrations of same.

Referring more particularly now to FIGS. 30 and 31, the inventors have discovered that by measuring the formation of virus protein P24 within the cell it is possible to show that the virus protein synthesis is reduced in totally infected (clone cultures) treated with melittin. This means, in essence, that the effect of melittin (Seq. ID NO:1) on the virus is to attack the virus before it is released from an infected cell although it is possible that a reduction in virus numbers may be possible during and immediately after the addition of melittin to a cell culture or otherwise. However, the present evidence indicates that virus production takes approximately 3 to 5 days to reach its maximum after initiation of the culture. At this point in time, melittin is absent from the culture. Moreover, the test results obtained show that melittin has a half-life of 19 hours and is not measurable in the medium two hours after addition to the culture, that is, it is taken up by the cells. This observation excludes any effect in the experiments to be explained by a direct effect of melittin on "cell free" virus, that is, virus released into the supernatant.

The effect of repeated administration of hymenoptera venoms was investigated in mice. Groups of 10 NMRI mice (5 of each sex) were subcutaneously given the following venoms: honey bee, yellow jacket, hornet mixture or vespid mixture days 0, 4, 7, 12, 14 and 16. Each animal was also administered 1, 2.5, 5, 10, 25 and 50 µg of venom, respectively. Thereafter each animal received five monthly injections of 50 µg of venom. A fifth group was given a control solution and served as controls. The data is summarized in FIGS. 35 through 41A, respectively. Clinical observations and body weight registrations were repeatedly performed. At the termination of the experiment all animals were autopsied and a histopathological examination was performed. From the results of the investigation it was concluded that the mice tolerated the four venoms very well. No serious growths or microscopic changes were found.

MATERIALS AND METHODS EMPLOYED FOR THE PROLONGED TOXICITY STUDY UTILIZING VARIOUS HYMENOPTERA VENOMS

Introduction

To assess the effect of repeated administration of hymenoptera venoms on mammals, a prolonged toxicity study was carried out on mice.

Test Substances

Venoms from the following hymenoptera species were tested:

Honey bee (*Apis mellifera*) (ref. Nr. BV 02)

Yellow jacket (*Vespula maculifrons*) (Ref. Nr. YJ 02)

Hornet Mixture (White-faced hornet (*Vespula maculata*) and Yellow hornet (*Vespula arenaria*)) (ref. nr. MH 01)

Vespid Mixture (Yellow Jacket, White-faced hornet and Yellow hornet) (ref. No. MV 02).

The control animals received the following control solution:

NaCl: 0.12M

Human serum albumin (HSA): 0.03%

Mannitol: 3%

Sodium phosphate: 0.005M pH 7.4

Substance Preparation

The venoms were diluted in Evans' buffered saline:

$Na_2HPO_4$ $2H2O·2H_2O$—0.711 g/L $KH_2PO_4$—0.363 g/L

NaCl—5 g/L

Phenol—4 g/L di-Na-EDTA·$2H_2O$—0.1 g/L

Ph 7 different concentrations and in order to preserve the same dosage volume at each time, i.e. 0.5 ml/animal. The substances were prepared freshly at each administration.

Animals and Conditions

Animals: mice, NMRI strain, SPF (Anticimex, Norrviken), seven weeks old, weighing approx. 25 g (♀) and 30 g (♂) were housed 5 animals/cage. Diet: pellets (Anticimex, R3) and water ad libitum. Temperature (ambient): 22°±1° C. Humidity (relative): 50±10%. Light (artificial): 12 hours/day.

Group Size

Ten animals (five of each sex) were allocated, by random selection, to each of the five groups (including one control group).

| Group | Mice No. | Compound |
|-------|----------|----------|
| 1 | 1–10 | Controls |
| 2 | 101–110 | Honey Bee |
| 3 | 201–210 | Yellow Jacket |
| 4 | 301–310 | Hornet Mixture |
| 5 | 401–410 | Vespid Mixture |

Dosage

To each of the groups no. 2–5 the following dosage schedule was used:

| Day | 0 | 1 | µg | venom/animal |
|-----|---|---|-----|--------------|
| " | 4 | 2.5 | " | " |
| " | 7 | 5 | " | " |
| " | 12 | 10 | " | " |
| " | 14 | 25 | " | " |
| " | 16 | 50 | " | " |

Thereafter, each mouse received five monthly injections of 50 µg of the venom. The total amount of venom injected per mouse during the experimental period was thus 343.5 µg. The control animals followed the same time schedule but received at each opportunity 0.5 ml/animal of the control solution which had been diluted in Evans' buffered saline to contain the same relative concentrations of mannitol and HSA as group 2 and 3.

Route of Administration

Subcutaneously in the mid-dorsal, lumbar region.

Observations

Clinical Symptoms

Clinical symptoms of ill health or toxicity were controlled and recorded daily.

Body Weight

Individual body weight was recorded before onset of dosing and thereafter at each administration.

Terminal Studies

Six months after beginning the 50 µg injections all mice were sacrificed and autopsied. Tissues for histological preparation and histopathological examination were taken from the following organs; skin, salivary gland, trachea, lungs and bronchi, heart and aorta, thyroids, parathyroids, oesophagus, stomach, duodenum, jejunum, ileum, cecum, colon, mesenteric lymph nodes, liver, gallbladder, thigh muscle, sciatic nerve, sternebrae, thymus, pancreas, spleen, kidneys, adrenal, bladder, seminal vesicle, prostate, testes, ovaries, uterus, brain, pituitary gland, eyes, spinal chord, and injection sites.

Results

The results of the investigations are presented as individual data in FIGS. 35–41A.

Observations

Clinical Symptoms

Mouse no. 309 (Hornet Mixture) made continuous circular movements during the last two months of the experimental period.

Mouse no. 203 (Yellow Jacket) had edematous and sore fore legs with losing of the hair for a short period one month before the termination of the experiment.

Body Weight See FIGS. 36–40. Body weight was not influenced by the medication.

Terminal Studies

Gross Pathology

The spleen was firmly adherent to the abdominal wall in mouse no. 304 (Hornet Mixture) and to the pancreas in mouse no. 406 (Vesid Mixture). Mouse no. 101 and 105 (Honey bee) had each a firm, 1 mm nodule in their lungs. No other remarkable gross findings were made. The injection sites were at the time of sacrifice without swelling or other changes.

Microscopic Pathology

Figure 41:
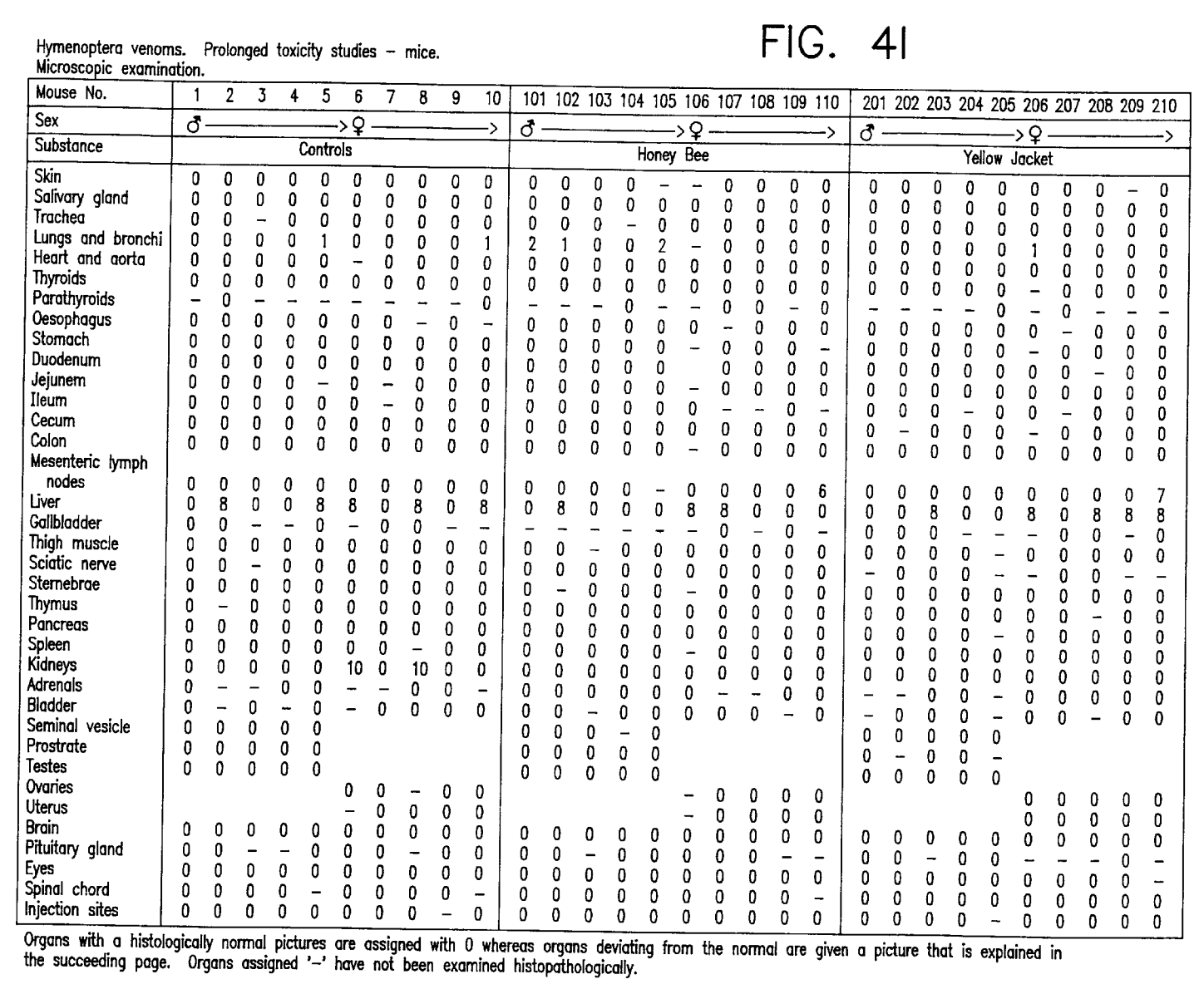

The results from the microscopic examination are presented in FIGS. 41 and 41A.

Reactive necrosis in the mesenteric lymph nodes were found in the following mice: no. 110 (Honey bee), no 307 and 308 (Hornet Mixture), no 406 and 410 (Vespid Mixture). In mouse no. 210 (Yellow Jacket) there was a moderately lymphoid hyperplasia in the mesenteric lymph node.

In mouse No. 310 (Hornet Mixture) there was a focal necrosis with a subacute or chronic cellular reaction in the spleen. In mouse no. 304 (Hornet Mixture) the adhesion from the spleen to the abdominal wall was found to be of a chronic fibrous nature and the adhesion from the spleen to the pancreas in mouse no. 406 (Vespid Mixture) was chronic fibrous and well vascularized.

The described changes in the mesenteric lymph nodes and in the spleens may have been induced by the venoms but they are judged to be of an innocent character relative to the animals' condition.

Small adenomas in the lungs were seen in mouse no. 101 and 105 (Honey bee) and in mouse no. 402 (Vespid Mixture). In mouse no. 407 (Vespid Mixture) there was a small nodular hyperplasia of bronchial epithelium. These types of changes occur spontaneously.

In the control mice as well as the mice given the venoms, there were occasionally findings of very small necrosis of hepatic parenchymal cells with slightly cellular infiltrations. Further, slight chronic inflammatory changes were seen in the kidneys in three control mice.

In Vivo Experiments on Rausher Leukemia Mice

The Rausher leukemia mice is a model for retroviral infections of mammals which is generally accepted. The virus produces an erythropoietic leukemia in mice which is revealed by an increase in the size of the spleen as an indication of increased production of red blood cells. The size of the spleen is taken as a measure of the progress of the disease which eventually leads to the death of the infected animals. The effect of the melittin-analogue with a tail of 6 gly was tested in this system.

EXAMPLE 1

The test of the antiviral effect of the melittin (Seq. ID NO:1) principle was carried out on Balb C mice (12 weeks old; all males). The animals were kept in numbers of 4 per cage. The animals were infected by Rausher leukemia virus ($10^5$ infectious particles (viruses) per animal in a volume of 0.2 ml) by intraperitoneal injection (ip) followed by subcutaneous injection of the test substance after 10 minutes. The animals were divided into two groups referred to as controls (receiving a sham injection of saline) or test animals (receiving the melittin analogue).

Two groups of balb C mice, each of 16 animals infected as described above, were injected with either phosphate buffered saline (25 mM $KH_2PO_4$, 150 mM naCl, pH 7.8, referred to as PBS), or with Melittin-6-gly (5 µg/mg body weight in a volume of 0.1 ml) in PBS. The peptide was dissolved as 100 µg/ml and the controls as well as the test animals were injected with the same volume subcutaneously (0.1 ml) of PBS or PBS+test substance respectively. The injection was carried out 10 minutes after injection of the infectious virus. After 2 days the animals received a new injection of melittin analogue (10 µg/mg body weight) or PBS as a subcutaneous injection of 0.100 ml. After 4 days from the first injection a third injection was performed using 20 µg/mg body weight of melittin analogue. All animals were unaffected by the injections of melittin analogue or PBS, and all survived the acute phase of the injections.

Normally infected mice will develop spleens with a weight higher than 150 mg within two weeks. The size can increase to 2.5 grams. The normal spleen is between 0.1 and 0.15 mg as lower and upper level, meaning that 95% of mice will have spleens within this range. A spleen greater than 170 mg was taken as a clear infection after two weeks, a spleen between the upper normal level of 150 mg, and 170 mg, was considered a borderline case. After 2 weeks all animals tested in the control group had developed spleens greater than 150 mg. In the test group, 25% of the tested animals had also developed spleens greater than 150 mg, but lower than 170 mg and were considered as borderline cases. However, the rest were showing no signs of enlargement of the spleen, that is, it was within 100–150 mg range which would be expected for normal animals. Only one animal had a spleen which was pathological as compared to 100% in the control group.

The following conclusions are drawn from these experiments.

1. The animals survive the treatment with melittin (Seq. ID NO:5–7 and 12) analogues in concentrations which are comparable to the in vitro experiments described in this patent application.
2. The melittin analogue clearly inhibits development of a retrovirus in mammals since 75% of infected animals do not develop disease as compared to 100% development of the disease in a comparably treated control group.
3. Not only HIV but also other retroviruses are inhibited by melittin (Seq. ID NO:1) and its analogues.

EXAMPLE 2

As noted earlier, the Rauscher leukemia virus (RLV) model has been used successfully to test a number of compounds like nucleoside analogues, that is, AZT, and which has been utilized, heretofore, to inhibit HIV replication. This is discussed in further detail in the article authored by R. M. Ruprechet, et. al. and which is entitled *Development of Antiviral Treatment Strategies in Murin Models*, RES. Human Retroviruses, 8,997-1011 (1992). Those skilled in the art will recognized that RLV belongs to the Onkoviruses, which is a subfamily of the retrovirus family, and not to the Lentiviruses family, such as is the case with HIV. Therefore, the RLV model provides a suitable basis upon which one may test substances which interfere with the replication steps which are common, or similar, among related retroviruses. As noted earlier, inasmuch as the melittin (Seq. ID NO:1) appears to inhibit HIV transcription in vitro, then it appears that RLV is a suitable model to test the effect of melittin on in vivo replication inhibition.

Materials and Methods

The source of virus for the present example was secured from the leukemic spleens of RLV infected Balb/c mice. The virus titer of the pool of leukemic spleens was determined by titration. This titration method is discussed in the article authored by Schmidt et al., "Endogenous Murine Leukemia Viruses: frequency of radiation-activation and novel pathogenic effects of viral isolates." Leukemia Research 12, 393–403, (1988). The spleens were secured from 8 to 10 week old inbreed female Balb/c mice, and further from in mouse embryo fibroblasts. As noted earlier, virus replication in mice normally has been determined by the development of leukemia in the spleen. Additionally, the determination of in vitro virus replication has been measured heretofore by the number of virus protein producing cells which are stained with anti-RLV antibodies in an immuno-peroxidase staining test (IPF). Aliquots of the virus solutions were stored in liquid nitrogen and were again titrated in the fashion as noted above.

Figure 48:
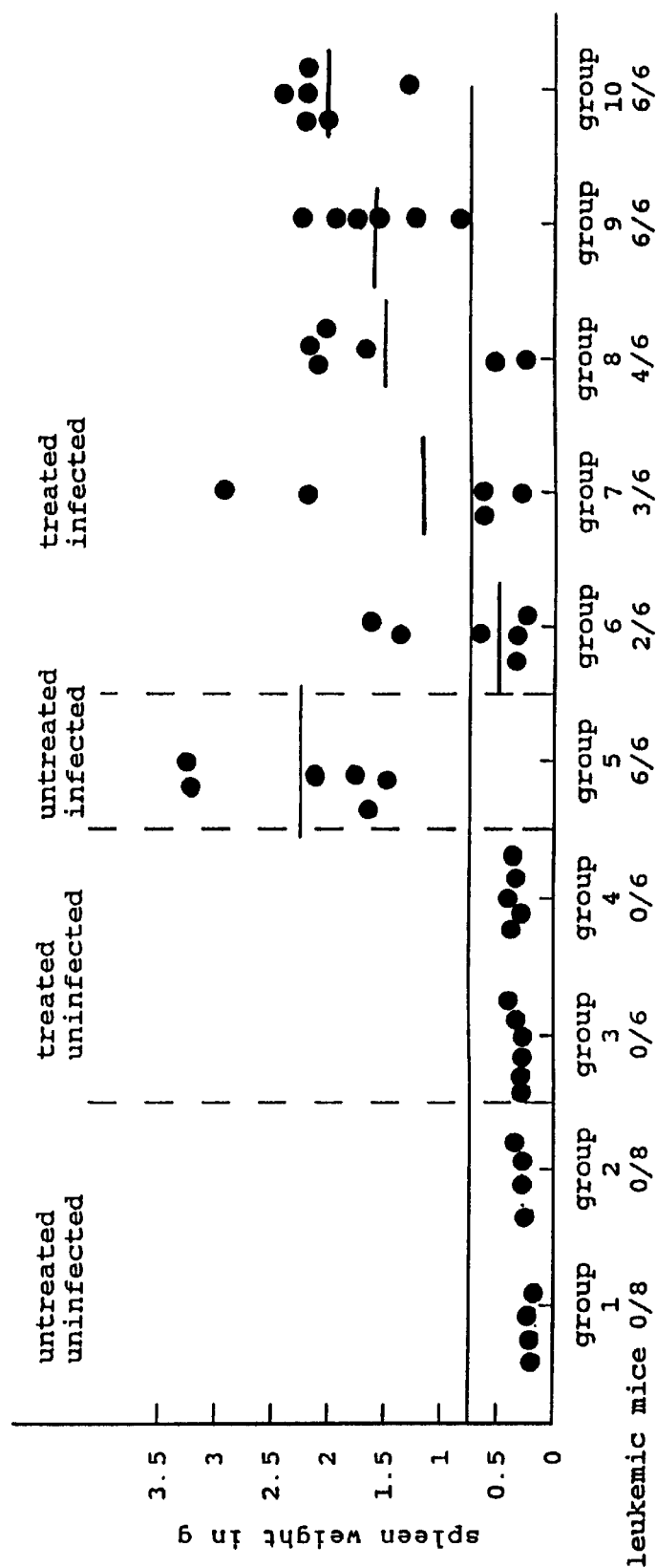
FIG. 48 is a graphic representation of the information disclosed in FIG. 43.

Stock virus solutions were diluted to provide solutions having a virus concentration of approximately $7 \times 10^6$ infectious units per milliliter. Following preparation of the solutions, 0.5 ml of these viral solutions were injected intraperitoneally (ip) into Balb/c mice that were 8 to 10 weeks old. These particular animals had a median body weight of approximately 20 to 25 grams, and a mean spleen weight of approximately 0.14 to 0.16 grams, respectively. As will be recognized by a study of FIG. 43 and FIG. 48, and following infection with the RLV, nearly 100% of the mice developed leukemia (splenomegaly) within approximately three weeks. These infected mice had a spleen weight of approximately 4 grams. The mean spleen weight development became less prominent. This is best seen by reference to FIG. 48 and in particular groups 8, 9 and 10.

Figure 49:
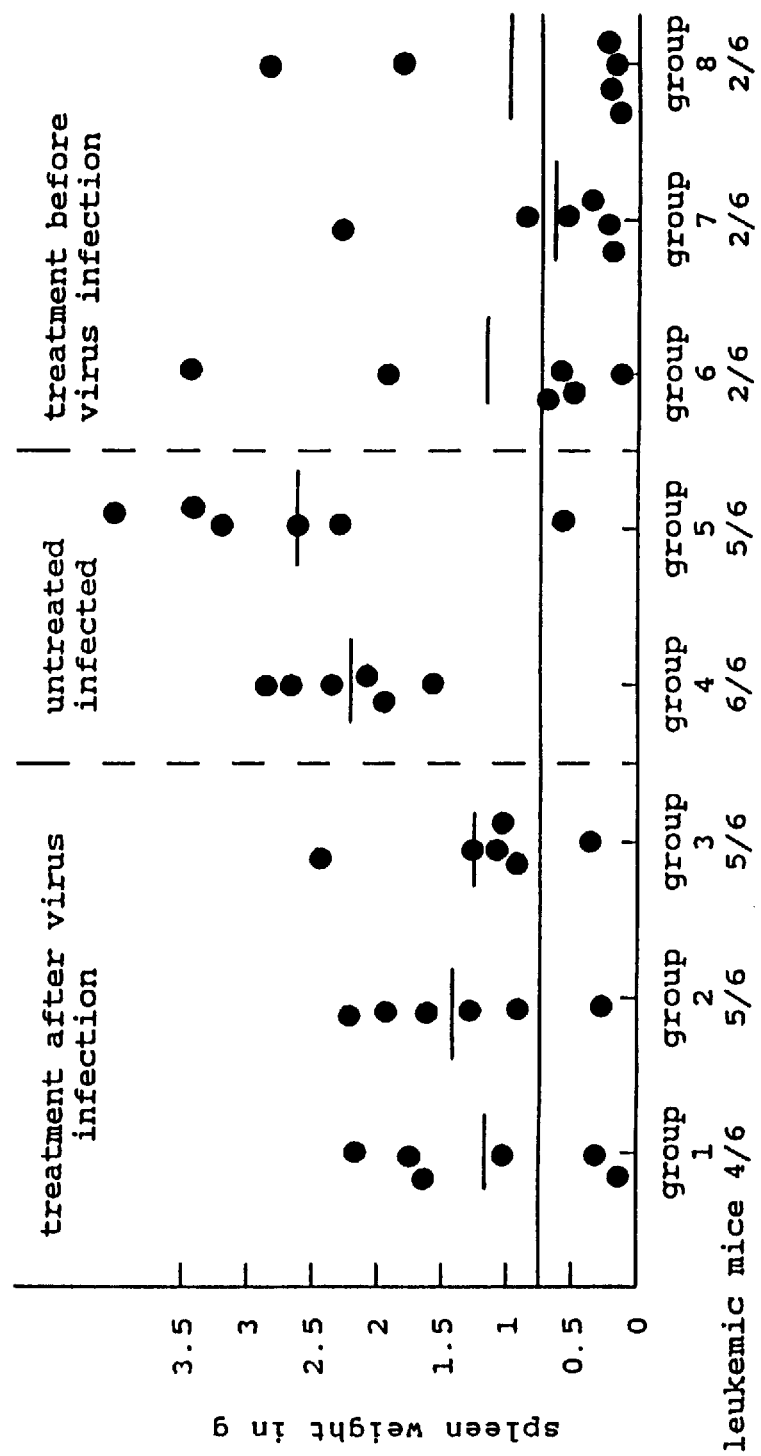
FIG. 49 is a graphic illustration of the information disclosed in FIG. 44.

Referring now to FIG. 44 and FIG. 49, the same animals noted above were tested for the effects of melittin (Seq. ID NO:1) application both before, and after, infection with RLV. As best seen in FIG. 44, the two untreated groups, that is groups 4 and 5; all 6 of the mice in group 4; and 5 of the 6 mice in group 5 developed leukemia which manifested itself with a mean spleen weight of 2.3 and 2.7 grams, respectively. In contrast, and following melittin application after infection (groups 1, 2 and 3) the melittin reduced the number of leukemic animals to 4 out of 6 in group 1; 5 out of 6 in group 2; and 5 out of 6 in group 3, respectively. These animals had mean spleen weights of 1.1 grams, 1.3 grams and 1.1 grams, respectively. There appeared to be no major difference in the clinical effect of the melittin administration, that is, whether it was administered in intervals of 4 days (group 1); 2 days (group 2); or daily (group 3). When melittin was administered in a single injection before infection, the effect on leukemia development appeared even more pronounced. In the case of the 3 groups, group 6 (12 hours before), group 7 (24 hours before) and group 8 (6 hours before), the total number of leukemic animals that were located after three weeks was reduced to 2 animals out of the 6 tested. The mean spleen weight was also reduced to 1.1 grams; 0.7 grams; and 0.9 grams, respectively.

Figure 50:
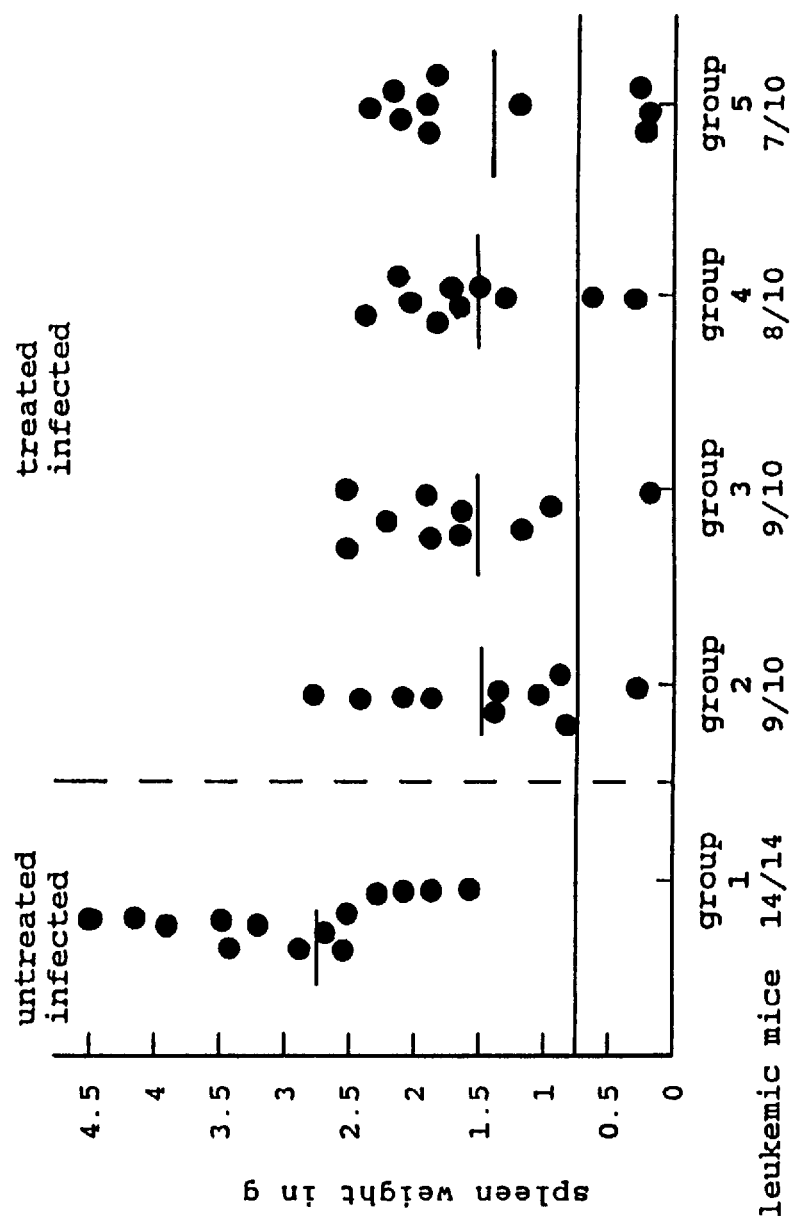
FIG. 50 is a graphic illustration of the information disclosed in FIG. 45.

As best seen by reference to FIGS. 45 and 50, respectively, the solutions, as noted earlier, were utilized in a series of experiments where the effect of preinfection treatment was evaluated in more detail. In the case of the RLV infected mice, all of the mice (14 out of 14) developed leukemia within three weeks, with a mean spleen weight of 2.8 grams. Furthermore, nearly all of the pre-treated animals also developed leukemia, but these had a reduced mean spleen weight: 1.5 grams (group 2 having received 5 injections); 1.5 grams (group 3 having received 4 injections); and 1.3 grams (group 4 having received 3 injections). These results were quite similar to group 5 which were treated with melittin (Seq. ID NO:1) once before infection, and five times later in four day intervals. In these particular animals, the treatment resulted in a mean spleen weight of approximately 1.3 grams.

Figure 51:
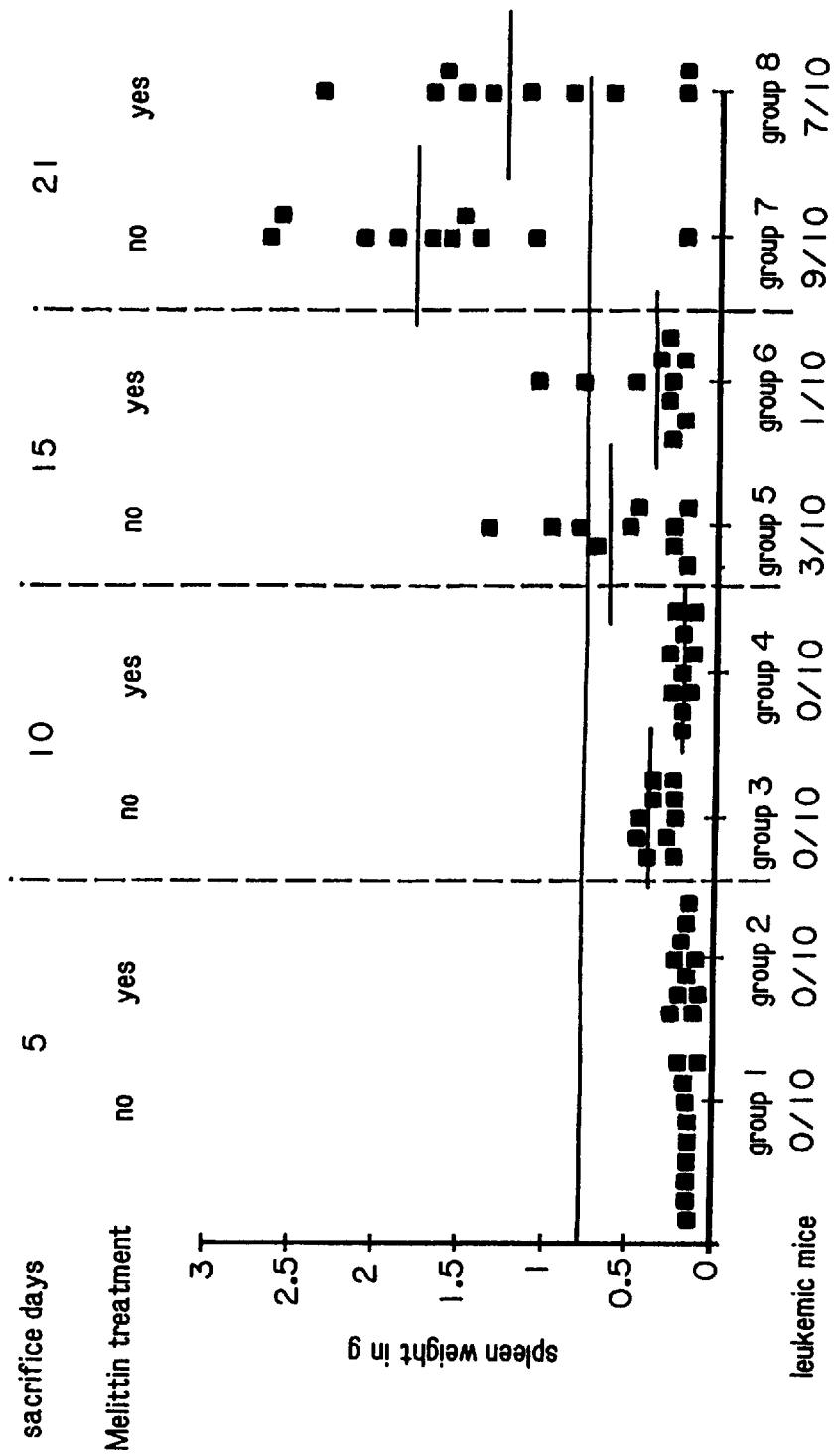
FIG. 51 is a graphic illustration of the information shown in FIG. 46.
Figure 52:
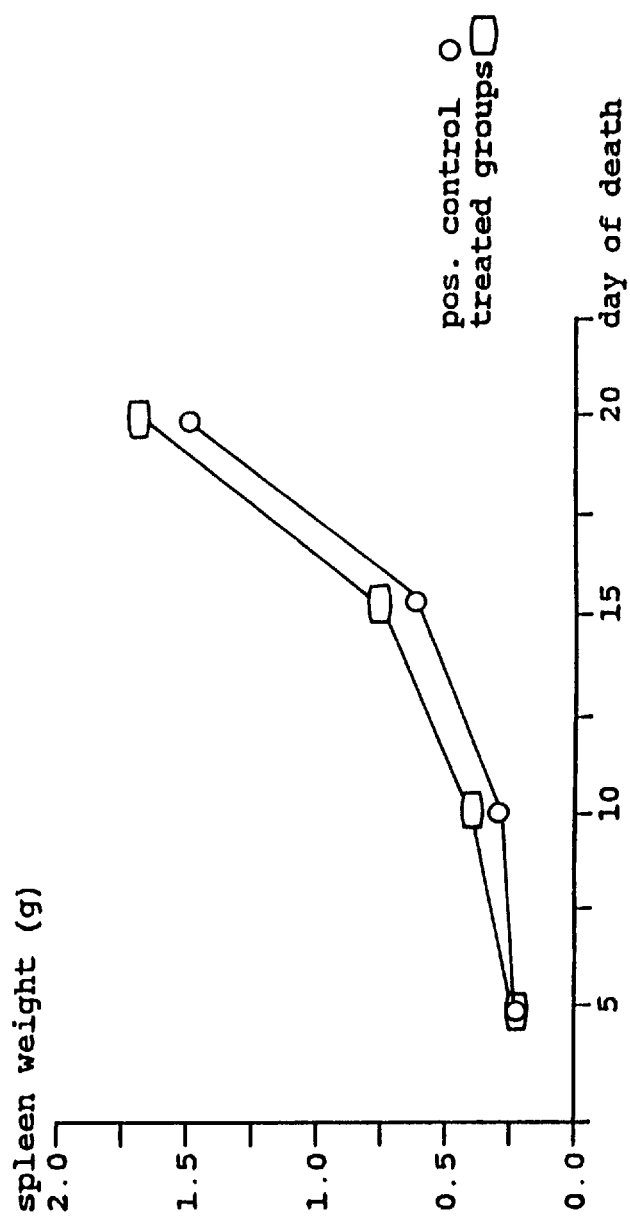
FIG. 52 is a graphic illustration of the information shown in FIG. 46.

Turning now to FIG. 46 and FIG. 51, respectively, in this series of experiments, the course of the leukemia infection over time, and spleen weight development of RLV infected mice was observed, in parallel, in both melittin (Seq. ID NO:1) treated, and untreated groups of mice. Spleen weight determinations were made on days 5, 10, 15 and 21 with groups of 10 animals being sacrificed. Melittin was administered on five occasions before, and six occasions after, infection. At time intervals of five and ten days respectively, the spleen weights of the treated and untreated mice appeared to be quite similar with only a slight difference appearing on day 10. Analysis of these animals indicated that no leukemic animals could be found on days 5 and 15. However, a few leukemic animals on day 15 appeared, and there appeared to be a slight difference in the spleen weight in the two groups. In this regard, the untreated group, that is group 5, had three leukemic animals out of a total of ten analyzed; and the treated group (group 6) only had one leukemic animal. The experiment was completed at day 21, and an analysis of the mice on that day indicated that in the untreated group, (group 7), 9 out of 10 animals analyzed developed leukemia with a mean spleen weight of approximately 1.7 grams. In contrast, the melittin treated group (group 8) only had 7 out of 10 animals develop leukemia with a mean spleen weight of 1.2 grams. This is best seen in FIG. 46.

In summary, it appears that in all the treated groups, regardless of the treatment schedule, only 70% of the animals (81 of a total of 116 animals analyzed) developed leukemia with a mean spleen weight of 1.2 grams. In contrast, 95% of the untreated infected mice (40 out of 42 analyzed) were leukemic after three weeks of observation time with a mean spleen weight of 2.4 grams.

EXAMPLE 3

To further investigate the effects of melittin (Seq. ID NO:1) on virus replication in retroviral infected cells or the inhibition of retroviral infected cell growth, a series of experiments were conducted utilizing cats which were naturally infected with the feline immunodeficiency virus (FIV). FIV is in its genomic and viral structure, in many respects, very similar to the human immunodeficiency virus (HIV). Therefore, it is widely regarded as similar to HIV, that is, it is a member of the Lentivirus subfamily, of the retrovirus family. Further, it has been determined that experimentally and naturally infected cats having FIV, display very similar disease characteristics such as immunedysfunction or other neurological disorders which can be taken as a relevant model for HIV infection in humans. This is discussed in greater detail in the article authored by Egberink et. al. "Suppression of feline immuno-deficiency virus infection in vivo by 9-(2-phosphonomethoxyethyl)adenine," Proc. Natl. Acad. Sci. 87, 3087–3091 (1990).

Methods and Materials

Figure 53:
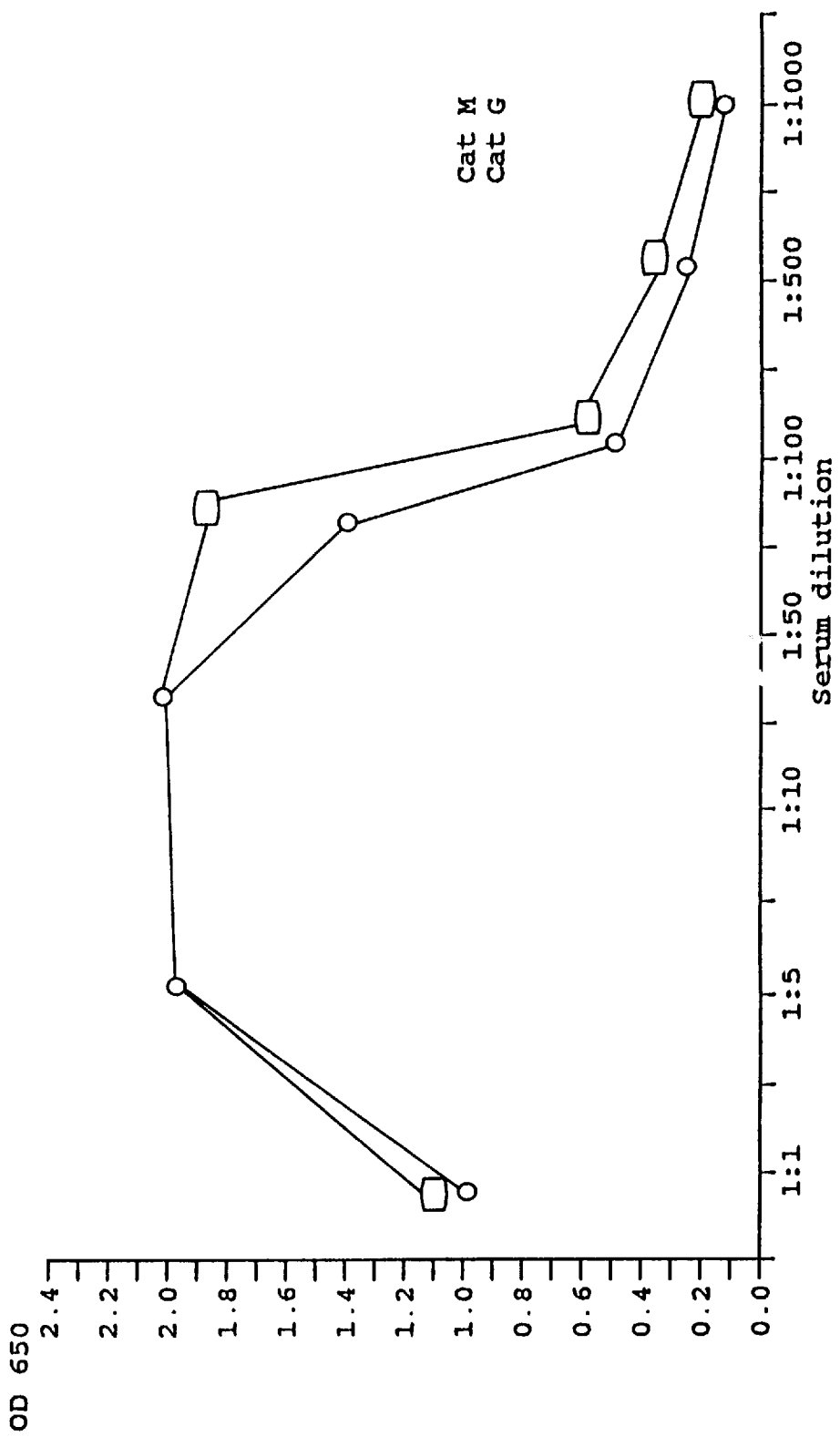
FIG. 53 is a graphic illustration of the information shown in FIGS. 47B and C, respectively.

In the following series of experiments, two naturally FIV infected cats (M and G) were used. These particular cats were kept for more than one year under constant observation in the Clinic for Internal Medicine at the Veterinary School in Munich, Germany before the onset of melittin (Seq. ID NO:1) treatment. In each cat, FIV infection had been confirmed by detecting an antibody ELISA. In this regard, a test marketed under the tradename PetChek® and which is available from the same company in Portland, Maine was employed. As best seen in FIG. 53. The antibody titer against FIV in both cats was approximately 1:50. As a general matter, the overall physical condition of both cats was good during the observation period. Further and during the experiment, cat M developed shortly before melittin treatment a pneumonitis which was not treated in a conventional fashion. The individual body weights of each cat at the beginning of melittin treatment was 4 kilograms and 2.2 kilograms for cats M and G, respectively.

Melittin (Seq. ID NO:1) was commercially purchased from ALK laboratories in Denmark. The melittin was purified from honey bee venom by reverse phase HPLC using a linear gradient of acetonitrile in 0.1% trifluroacetic acid (0–80% acetonitrile on a PepS 5uCl8 preparative column (22.5×250 mm) and which is commercially available from Pharmacia of Sweden. The gradient of from 0 to 80% acetonitrile was eluted over a period of 60 minutes at a flow rate of 10 ml/min. This resulted in a substance having more than 96% purity. Prior to utilization, the melittin was tested for HIV-1 replication inhibition, in vitro, by utilizing the procedure described in the article authored by Torben Saemark et al., entitled *Influence of Amphipathic Peptides on the HIV-1 Production in Persistently Infected T-Lymphoma Cells*, FEBS letters 309[3]: 235–241, (1992). This test includes measuring the release and infectivity of HIV from persistently infected lymphoma cells in the absence and presence of melittin by adding cell-free supernatant from the cell cultures to uninfected cultures followed by a determination of the number of infected cells by immunostaining using an antiserum against HIV particles. Only those batches of melittin having an anti-HIV-1 activity comparable to synthetically produced melittin were used in the in vivo trials.

During the experiment it was determined that detectable blood serum levels of melittin (Seq. ID NO:1) of about 5 ng/ml could be detected following an injection of melittin equal to 200 mg/kg a few minutes after injection. As a general matter, melittin disappears quickly from the serum. In vitro data has shown that melittin, after this time interval, is found within the cells where it can be detected in tact for more than 48 hours. The LD50 (lethal dose where 50% of the animals perish) for melittin is not known for cats. In the present experiment, both cats M and G were treated twice weekly with subcutaneous injections over a period of eight weeks. During the first three weeks, each cat received increasing dosages of melittin (Seq. ID NO:1) beginning with a 50 mg/kg bodyweight injection, followed by injections of 100 mg/kg, and then escalating to 150, 225, 375 and 500 mg/kg at the sixth injection. Upon reaching this level, the melittin was administered in a constant dosage of 500 mg/kg twice weekly, for the remaining five weeks. The individual cats appeared to tolerate the numerous injections without any clinically noticeable negative reactions. The quantitative effect of melittin on FIV replication was determined quantitatively by utilizing FIV-PCR employing nested primers from the gag region. Quantification was based upon the determination of amplified product in identical samples which have been amplified after different cycle times. This is best seen by reference to FIG. 47A. Furthermore, each of the cats were clinically investigated in detail. The specifics regarding the use of PCR and nested primers, and the quantification by PCR for HIV are set fourth in the articles to Ehrlich, A.: "PCR Technology: Principles and applications for DNA amplification", Stockton Press, New York, 1989; Innis, M. A., Gelfand, D. H., Sninsky, J. J., White, T. J.: "PCR Protocols, A guide to methods and applications"; Academic Press, Inc., San Diego, 1990; Poznansky, M. C., Walker, B., Haseltine, W. A. Sodroski, J., Langhoff, E.: "A rapid method for quantitating the frequency of peripheral blood cells containing HIV-1 DNA"; J. Acq. Immun. Def. Synd. 4, 368–373, 1991; and Bell, J., Ratner, L.: "Specifity of polymerase chain reactions for the human immunodeficiency virus type I DNA sequences"; AIDS Res Hum Retrovirus 5, 87–95, 1989. The substance of each of these articles are incorporated by reference herein.

The viral load of each of the FIV infected cats was determined by PCR. Blood was withdrawn for Quantitative PCR at the initiation of the experiment, and then at days 14, 28, 42, 56 and 116. DNA from the blood lymphocytes (buffy coat) was prepared from 3 mls of heparinized blood and 1 mg per sample, and tests of the resulting DNA were utilized in the evaluation. The amplified products were separated by agarose gel-electrophoresis and thereafter photographed under ultra-violet light using a pixel sychronous monochrome CCD camera such as the camera marketed under the tradename XC 77/PS and which is manufactured by Leutron Vision, of Germany. Further, a real time frame grabber was employed in combination with the camera. The frame grabber is manufactured by the same company. Samples were then screened with a video camera and then blotted on nitrocellulose filters for the subsequent hybridization analysis. The intensity of the bands in the UV light exposures are determined by a proprietary software program which is provided by the manufacturer of the camera noted above. To verify the nature of the amplified bands, southernblot hybridization was performed with a FIV specific probe. The probe employed was the FIV probe identified at position 1051–1089 of the disclosed sequence of the FIV-provirus as shown in the reference authored by G. Meyers, and which is entitled "Human Retrovirus and Aids"; Theoretical Biology and Biophysics, New Mexico, 1990. The procedure for implementation of the southernblot hybridization is disclosed in the article authored by Sambrook et al, and which is entitled "Molecular Cloning: A Laboratory Manual"; Cold Spring Harbour Press, 2nd Edition, New York, N.Y. 1989.

The evaluation of the amplified standard samples which comprise DNA from a FIV infected cell line containing one integrated FIV genome shows that 25 cycles of amplification leads to saturation of the reaction in all samples (FIG. 47A). Consequently, decreasing cycle times result in decreasing optical densities of the bands in the samples from higher dilutions. This is best illustrated by reference to FIG. 47A. The amplification of all DNA samples from cats M and G were done in one experiment in order to achieve good comparability. Further, the amplification was repeated on two other occasions, each of the experiments producing the same results. The results revealed that the amplification of FIV specific sequences in cat M resulted in similar results in the samples from days 1, 14, 28 and 42. The samples of days 56 and 116 showed a reduced amplification. This corresponded at least to a 50% reduction of the virus load. In cat G, a reduced amplification could already be seen in the sample from day 42 and the following days. The results of the densitometry are shown in FIGS. 47B and 47C. During the entire treatment, no adverse reaction or clinical abnormalities could be observed in either animal. Pneumonitis in cat M improved during the melittin treatment.

Conclusions

The overall impression from each of the examples noted above was that the mice tolerated the four venoms, that is, Honey bee, Yellow Jacket, Hornet Mixture and Vespid Mixture very well when administered same in small dose regimens. No serious gross or microscopic changes were found.

As earlier discussed, it appears that melittin presents a method for the treatment of HIV infections in mammals by perhaps interacting with one of the major HIV proteins, that is the glycoprotein GP41. This is possible because of the similarity between the transmembrane regions of GP41 and melittin and which is best shown by reference to FIG. 5.

As shown in FIG. 5, GP41 has an amphiphilic portion which may be a prominent feature of the membrane associated part of the molecule. The amphiphilic part of the GP41 may form an antiparallel loop of charged amino acids where the two legs of the loop form a charged neutralizing structure which is similar to the structure associated with the polymerization of melittin. Melittin (Seq. ID NO:1) may also prevent the normal formation of intramolecular charge neutralization by GP41 and thereby dramatically change the structure of GP41. This may affect the formation of the virus since formation of the virus appears to be dependent on the interaction of GP41 with the nucleus of the viral protein P17, and which is able to perform the basic viral budding process. As should be understood, viruses such as HIV spread from cell to cell by a process which involves formation of a small membrane bud on the cell surface and which contains the viral genome. This process seems to be sensitive to modifications of the cell surface. It is well known, for example, that addition of lipid formulations prevent the release of virus from infected cells. This effect is possibly due to a chaotropic action on the cell membrane. However, the mechanism of this action is still unclear.

The structural features of protein GP41 which permits melittin (Seq. ID NO:1) to interact with same appears to be located between amino acids 770 and 856 and involves the amphiphilic sequences 770 through 794 and 824 through 856. Please see FIG. 5. The amphiphilicity of these sequences was detected by their high hydrophobic momentum combined with a low overall hydrophobicity. The two amphiphilic legs have been modeled by molecular dynamics and they have been shown to be able to interact on the basis of their amphiphilicity and thereby potentially enable them to insert into the membrane by forming a transmembrane loop. Alternatively, they may float on the internal surface of the cell membrane. In either case, an interaction with melittin (Seq. ID NO:1) may cause a changed localization of the site of the cytoplasmeric part of GP41 thereby preventing the interaction with P17 which seems to be a necessary precursor for virus formation. In this regard, an interesting analogy between melittin and GP41 amphiphilic sequence 824 through 856 is that they both have a proline in the amphiphilic helix. This structural feature, as earlier discussed, introduces a 120° kink in the helix thus causing it to have a slightly bent form. Alternatively, melittin may interact with the membrane thus acting as a chaotropic agent. This also may be due to its amphiphilic nature. As should be understood, the effects of chaotropic agents are to cause a perturbation of the ordered phospholipid arrangement in the membrane. Such effects cause changes in the phase transition points of the membranes and subsequent changes in their thickness. As could be expected, the fact that floating melittin causes a chaotropic affect on the cell membrane is not surprising. However, and how this same event effects the budding process of the virus is unclear and not known at present. There are, however, strong indications of anti-HIV effects or changes induced in the order of the membrane lipid arrangement. Furthermore, addition of various phospholipid formulations also prevent HIV release from infected cells. It has not been possible, however, to identify the lipid species which causes for this effect.

Melittin (Seq. ID NO:1) is, however, known to interact with phospholipids, and this effect, or the binding, of an unidentified lipid species appears to be a function in HIV release and may also offer an explanation for the antiviral effect of melittin. Presumably this lipid is not a phospholipid since addition of phospholipids have an effect very similar to melittin.

The test results set forth in Examples 2 and 3 further illustrate that the prevent invention is useful in the treatment of HIV infections in man. The earlier disclosed experiments utilized the Rauscher Leukemia Virus Model (RLV) which has been used successfully to test a number of compounds like nucleoside analogues (AZT); and the Feline Immunodeficiency Virus (FIV) in cats which causes a similar immunodysfunction or neurological disorder which has been accepted as a relevant role model for the HIV infection in man. These two examples reveal that melittin (Seq. ID NO:1) treated animals showed improvement in comparison to untreated animals, as in the case of RLV model; and a 50% reduction in virus load, as was the case of the FIV model.

In conclusion, these test results appear to indicate that melittin (Seq. ID NO:1) has two effects, that is, it appears to have a first short term inactivation of the virus and a second long term reduction of at least P24 production. These characteristics appear to be due to the specific structure of the melittin amphiphilic helix. Further, the test information indicates that the tail structure determines the effectivity of an analog but not the quality of its effect, that is, the effective concentration of an analogue with a tail which includes Lys-Arg-Lys-Arg-Gly-Gly at its tail is about a hundred times lower than the effective concentration of no-tail melittin. In addition to the foregoing, the test results indicate that supernatant infectivity was reduced following a single treatment with melittin at subtoxic concentrations. In this regard, treatment was at cultivation start, and measurement of infectivity was seven days post treatment. As was discussed earlier, maximum virus concentration in cultures of this type is not achieved for five days after cultivation. As should be understood and the conclusions which the inventors have drawn from same is that if the reduced viral infectivity seven days post treatment were only due to direct effects of melittin on the virus, then in that event, the melittin or an active fragment would have to be present as late as five days post treatment. This is not possible inasmuch as the inventors have discovered that melittin is absorbed by the cell within hours after introduction to the culture. Moreover, and if the reduction and supernatant infectivity was partly due to reduced virus production as opposed to incorrect virus assembly or destruction of newly synthesized virion, then, in that event, this should be reflected by reduced amounts of viral proteins within the cells and/or in their supernatants of the melittin treated cultures. To determine whether this hypothesis is correct the inventors chose the P24 marker as a marker for viral protein production. The test data shows that there is, if at all, only a slight reduction of cellular and supernatant P24 following three hours of incubation with melittin. However, following fourteen hours of incubation with melittin, there is a marked reduction of P24 within the cells as well as in the supernatant (down to 60%). Therefore, cellular P24 seems to be reduced sooner and more strongly than supernatant P24. Moreover, incubation of cell free HIV with melittin does not impair the detection of the P24 antigen. It rather only appears to cause the virus infectivity to be reduced.

Although the invention has been herein shown and described in what is conceived to be the most practical and preferred embodiment it is recognized that departures may be made therefrom within the scope of the invention which is not to be limited to the illustrative details disclosed.

SEQUENCE LISTING ( 1 ) GENERAL INFORMATION:

( i i i ) NUMBER OF SEQUENCES: 12

( 2 ) INFORMATION FOR SEQ ID NO:1:

(i) SEQUENCE CHARACTERISTICS:
    (A) LENGTH: 26 AMINO ACIDS
    (B) TYPE: AMINO ACID
    (D) TOPOLOGY: LINEAR (ii) MOLECULE TYPE: PEPTIDE (ix) FEATURE:
    (A) NAME/KEY: melittin
    (B) LOCATION: whole molecule
    (C) IDENTIFICATION METHOD: by experiments on HIV release
        from human LC5 cells and sequence similarity to gp41
        from Human Immunodeficiency Virus (hiv).
    (D) OTHER INFORMATION: melittin is the main component in
        honey bee toxin and is able to lyse red blood cells.

(x) PUBLICATION INFORMATION:
    (A) AUTHORS: Wachinger, Michael, Saermark,Torben &
        Erfle,Volker.
    (B) TITLE: Influence of amphipathic peptides on the HIV-1
        production in persistently infected T-lymphoma cells.
    (C) JOURNAL: FEBS letters
    (D) VOLUME: 309
    (E) ISSUE: 3
    (F) PAGES: 235-241
    (G) DATE: spring 1992.

(ix) SEQUENCE DESCRIPTION: SEQ ID NO: 1:

Gly Ile Gly Ala Val Leu Lys Val Leu Thr Thr Gly Leu
1               5                   10

Pro Ala Leu Ile Ser Trp Ile Lys Arg Lys Arg Gln Gln
    15                  20                  25

(2) INFORMATION FOR SEQ ID NO:2:

(i) SEQUENCE CHARACTERISTICS:
    (A) LENGTH: 26 AMINO ACIDS
    (B) TYPE: AMINO ACID
    (D) TOPOLOGY: LINEAR (ii) MOLECULE TYPE: PEPTIDE (ix) FEATURE:
    (A) NAME/KEY: melittin acid
    (B) LOCATION: whole molecule
    (C) IDENTIFICATION METHOD: Modification of the C-terminus of
        native melittin, which was identified as an antiviral
        compound by experiments on HIV release from human LC5
        cells and sequence similarity to gp41 from Human
        Immunodeficiency Virus (hiv).
    (D) OTHER INFORMATION: melittin is the main component in
        honey bee toxin and is able to lyse red blood cells.
        This analogue is a C-terminal acid prepared to study
        the importance of the structure of the C-terminal part
        of the molecule on HIV release.

(x) PUBLICATION INFORMATION:
    (A) AUTHORS: Wachinger, Michael, Saermark,Torben &
        Erfle,Volker.
    (B) TITLE: Influence of amphipathic peptides on the HIV-1
        production in persistently infected T-lymphoma cells.
    (C) JOURNAL: FEBS letters
    (D) VOLUME: 309
    (E) ISSUE: 3
    (F) PAGES: 235-241
    (G) DATE: spring 1992.

(ix) SEQUENCE DESCRIPTION: SEQ ID NO: 2:

Gly Ile Gly Ala Val Leu Lys Val Leu Thr Thr Gly Leu
1               5                   10

Pro Ala Leu Ile Ser Trp Ile Lys Arg Lys Arg Gln Gln
    15                  20                  25

(2) INFORMATION FOR SEQ ID NO:3:

( i ) SEQUENCE CHARACTERISTICS:
   ( A ) LENGTH: 26 AMINO ACIDS
   ( B ) TYPE: AMINO ACID
   ( D ) TOPOLOGY: LINEAR ( i i ) MOLECULE TYPE: PEPTIDE ( i x ) FEATURE:
   ( A ) NAME/KEY: melittin 6
   ( B ) LOCATION: whole molecule
   ( C ) IDENTIFICATION METHOD: Modification of the C-terminus of
       native melittin, which was identified as an antiviral
       compound by experiments on HIV release from human LC5
       cells and sequence similarity to gp41 from Human
       Immunodeficiency Virus (hiv).
   ( D ) OTHER INFORMATION: melittin is the main component in honey bee toxin and is able to lyse red blood cells. This analogue is a C-terminal modification prepared to study the importance of the positive charges on the C-terminal part of the molecule on HIV release.

( x ) PUBLICATION INFORMATION:
( A ) AUTHORS: Wachinger, Michael, Saermark,Torben & Erfle,Volker.
( B ) TITLE: Influence of amphipathic peptides on the HIV-1 production in persistently infected T-lymphoma cells.
( C ) JOURNAL: FEBS letters
( D ) VOLUME: 309
( E ) ISSUE: 3
( F ) PAGES: 235-241
( G ) DATE: september 14, 1992.

( i x ) SEQUENCE DESCRIPTION: SEQ ID NO: 3:

Gly Ile Gly Ala Val Leu Lys Val Leu Thr Thr Gly Leu
1 5 10

Pro Ala Leu Ile Ser Trp Ile Lys Lys Lys Lys Gln Gln
15 20 25

( 2 ) INFORMATION FOR SEQ ID NO:4:

( i ) SEQUENCE CHARACTERISTICS:
( A ) LENGTH: 26 AMINO ACIDS
( B ) TYPE: AMINO ACID
( D ) TOPOLOGY: LINEAR ( i i ) MOLECULE TYPE: PEPTIDE ( i x ) FEATURE:
( A ) NAME/KEY: melittin 4
( B ) LOCATION: whole molecule
( C ) IDENTIFICATION METHOD: Modification of the C-terminus of native melittin, which was identified as an antiviral compound by experiments on HIV release from human LC5 cells and sequence similarity to gp41 from Human Immunodeficiency Virus (hiv).
( D ) OTHER INFORMATION: melittin is the main component in honey bee toxin and is able to lyse red blood cells. This analogue is a C-terminal modification prepared to study the importance of the charges on the C-terminal part of the molecule on HIV release.

( x ) PUBLICATION INFORMATION:
( A ) AUTHORS: Wachinger, Michael, Saermark,Torben & Erfle,Volker.
( B ) TITLE: Influence of amphipathic peptides on the HIV-1 production in persistently infected T-lymphoma cells.
( C ) JOURNAL: FEBS letters
( D ) VOLUME: 309
( E ) ISSUE: 3
( F ) PAGES: 235-241
( G ) DATE: september 14, 1992.

( i x ) SEQUENCE DESCRIPTION: SEQ ID NO: 4:

Gly Ile Gly Ala Val Leu Lys Val Leu Thr Thr Gly Leu
1 5 10

Pro Ala Leu Ile Ser Trp Ile Lys Arg Lys Arg Gly Gly
   15                  20                25

(2) INFORMATION FOR SEQ ID NO:5:

(i) SEQUENCE CHARACTERISTICS:
        (A) LENGTH: 26 AMINO ACIDS
        (B) TYPE: AMINO ACID
        (D) TOPOLOGY: LINEAR (ii) MOLECULE TYPE: PEPTIDE (ix) FEATURE:
        (A) NAME/KEY: melittin E
        (B) LOCATION: Analogue of whole molecule
        (C) IDENTIFICATION METHOD: Modification of the C-terminus of
            native melittin, which was identified as an antiviral
            compound by experiments on HIV release from human LC5
            cells and sequence similarity to gp41 from Human
            Immunodeficiency Virus (hiv).
        (D) OTHER INFORMATION: melittin is the main component in
            honey bee toxin and is able to lyse red blood cells. This
            analogue is a C-terminal modification prepared to study
            the importance of the charges on the C-terminal part of
            the molecule on HIV release.

(x) PUBLICATION INFORMATION:
        (A) AUTHORS: Wachinger, Michael, Saermark,Torben &
            Erfle,Volker.
        (B) TITLE: Influence of amphipathic peptides on the HIV-1
            production in persistently infected T-lymphoma cells.
        (C) JOURNAL: FEBS letters
        (D) VOLUME: 309
        (E) ISSUE: 3
        (F) PAGES: 235-241
        (G) DATE: september 14, 1992.

(ix) SEQUENCE DESCRIPTION: SEQ ID NO: 5:

Gly Ile Gly Ala Val Leu Lys Val Leu Thr Thr Gly Leu
 1           5                   10
Pro Ala Leu Ile Ser Trp Ile Gly Gly Gly Gly Gly Gly
   15                  20                25

(2) INFORMATION FOR SEQ ID NO:6:

(i) SEQUENCE CHARACTERISTICS:
        (A) LENGTH: 21 AMINO ACIDS
        (B) TYPE: AMINO ACID
        (D) TOPOLOGY: LINEAR (ii) MOLECULE TYPE: PEPTIDE (ix) FEATURE:
        (A) NAME/KEY: melittin F
        (B) LOCATION: analogue of amino acids 1-21
        (C) IDENTIFICATION METHOD: Modification of the C-terminus of
            native melittin, which was identified as an antiviral
            compound by experiments on HIV release from human LC5
            cells and sequence similarity to gp41 from Human
            Immunodeficiency Virus (hiv).
        (D) OTHER INFORMATION: melittin is the main component in
            honey bee toxin and is able to lyse red blood cells. This
            analogue is a C-terminal modification prepared to study
            the importance of the charges on the C-terminal part of
            the molecule on HIV release. The Amino Acid Xaa
            (i n d i c a t e d   b e l o w) is ornithine. Ornithine is a non-
            essential amino acid which is important in protein
            metabolism.

(x) PUBLICATION INFORMATION:
        (A) AUTHORS: Wachinger, Michael, Saermark,Torben &
            Erfle,Volker.
        (B) TITLE: Influence of amphipathic peptides on the HIV-1
            production in persistently infected T-lymphoma cells.
        (C) JOURNAL: FEBS letters (D) VOLUME: 309
(E) ISSUE: 3
(F) PAGES: 235-241
(G) DATE: september 14, 1992.

(ix) SEQUENCE DESCRIPTION: SEQ ID NO: 6:

```
Gly Ile Gly Ala Val Leu Lys Val Leu Thr Thr Gly Leu
1               5                   10
Pro Ala Ile Ser Trp Ile Xaa Xaa
    15              20
```

(2) INFORMATION FOR SEQ ID NO:7:

(i) SEQUENCE CHARACTERISTICS:
      (A) LENGTH: 20 AMINO ACIDS
      (B) TYPE: AMINO ACID
      (D) TOPOLOGY: LINEAR (ii) MOLECULE TYPE: PEPTIDE (ix) FEATURE:
      (A) NAME/KEY: melittin 1-20
      (B) LOCATION: amino acids 1-20
      (C) IDENTIFICATION METHOD: Modification of the C-terminus of native melittin, which was identified as an antiviral compound by experiments on HIV release from human LC5 cells and sequence similarity to gp41 from Human Immunodeficiency Virus (hiv).
( D ) OTHER INFORMATION: melittin is the main component in honey bee toxin and is able to lyse red blood cells. This analogue is a C-terminal modification prepared to study the importance of the charges on the C-terminal part of the molecule on HIV release.

( x ) PUBLICATION INFORMATION:
( A ) AUTHORS: Wachinger, Michael, Saermark,Torben & Erfle,Volker.
( B ) TITLE: Influence of amphipathic peptides on the HIV-1 production in persistently infected T-lymphoma cells.
( C ) JOURNAL: FEBS letters
( D ) VOLUME: 309
( E ) ISSUE: 3
( F ) PAGES: 235-241
( G ) DATE: september 14, 1992.

( i x ) SEQUENCE DESCRIPTION: SEQ ID NO: 7:

Gly Ile Gly Ala Val Leu Lys Val Leu Thr Thr Gly Leu
1 5 10

Pro Ala Leu Ile Ser Trp Ile
15 20

( 2 ) INFORMATION FOR SEQ ID NO:8:

( i ) SEQUENCE CHARACTERISTICS:
( A ) LENGTH: 26 AMINO ACIDS
( B ) TYPE: AMINO ACID
( D ) TOPOLOGY: LINEAR ( i i ) MOLECULE TYPE: PEPTIDE ( v ) FRAGMENT TYPE: internal fragment of the c-terminal part ( i x ) FEATURE:
( A ) NAME/KEY: Amfi 1
( B ) LOCATION: pos 823-848 of HIV (bru) gp41 from amino acids Gly-Thr-Asp to Arg-Gln-Gly
( C ) IDENTIFICATION METHOD: by experiments on HIV release from human LC5 cells and sequence similarity to melittin.
( D ) OTHER INFORMATION: melittin is the main component in honey bee toxin and is able to lyse red blood cells.

( x ) PUBLICATION INFORMATION:
( A ) AUTHORS: Wachinger, Michael, Saermark,Torben & Erfle,Volker.

(B) TITLE: Influence of amphipathic peptides on the HIV-1
production in persistently infected T-lymphoma cells.
(C) JOURNAL: FEBS letters
(D) VOLUME: 309
(E) ISSUE: 3
(F) PAGES: 235-241
(G) DATE: spring 1992.

(ix) SEQUENCE DESCRIPTION: SEQ ID NO: 8:

Gly Thr Asp Arg Val Ile Glu Val Val Gln Gly Ala Cys Arg
1               5                   10

Ala Ile Arg His Ile Pro Arg Arg Ile Arg Gln Gly
15              20              25

(2) INFORMATION FOR SEQ ID NO:9:

(i) SEQUENCE CHARACTERISTICS:
(A) LENGTH: 27 AMINO ACIDS
(B) TYPE: AMINO ACID
(D) TOPOLOGY: LINEAR (ii) MOLECULE TYPE: PEPTIDE (v) FRAGMENT TYPE: internal fragment of the c-terminal part (ix) FEATURE:
(A) NAME/KEY: Amfi 2
(B) LOCATION: pos 684-711 of HIV (bru) gp41 from amino acids
Phe-Ile- metto Arg-Gln-Gly
(C) IDENTIFICATION METHOD: by experiments on HIV release
from human LC5 cells and sequence similarity to melittin.
(D) OTHER INFORMATION: melittin is the main component in
honey bee toxin and is able to lyse red blood cells.

(x) PUBLICATION INFORMATION:
(A) AUTHORS: Wachinger, Michael, Saermark,Torben &
Erfle,Volker.
(B) TITLE: Influence of amphipathic peptides on the HIV-1
production in persistently infected T-lymphoma cells.
(C) JOURNAL: FEBS letters
(D) VOLUME: 309
(E) ISSUE: 3
(F) PAGES: 235-241
(G) DATE: spring 1992.

(ix) SEQUENCE DESCRIPTION: SEQ ID NO: 9:

Gly Gln Arg Val Arg Asn Val Ile Ser Leu Val Ala
1               5                   10

Phe Val Ile Arg Leu Gly Val Leu Gly Gly Val Ile Met Ile Phe
            15              20              25

(2) INFORMATION FOR SEQ ID NO:10:

(i) SEQUENCE CHARACTERISTICS:
(A) LENGTH: 20 AMINO ACIDS
(B) TYPE: AMINO ACID
(D) TOPOLOGY: LINEAR (ii) MOLECULE TYPE: PEPTIDE (v) FRAGMENT TYPE: internal fragment (ix) FEATURE:
(A) NAME/KEY: MHC
(B) LOCATION: pos 248 to 268 of Major Histocompatibility
complex from amino acids Val-Ala-Ala to Lys-Leu-Glu
(C) IDENTIFICATION METHOD: by calculation of amphiphilicity
using an Edmundson wheels and structural similarity to
melittin.
(D) OTHER INFORMATION: melittin is the main component in
honey bee toxin and is able to lyse red blood cells.
This molecule is a structural analogue of melittin
having a similar amphiphilic structure.

(x) PUBLICATION INFORMATION:
  (A) AUTHORS: Wachinger, Michael, Saermark,Torben & Erfle,Volker.
  (B) TITLE: Influence of amphipathic peptides on the HIV-1 production in persistently infected T-lymphoma cells.
  (C) JOURNAL: FEBS letters
  (D) VOLUME: 309
  (E) ISSUE: 3
  (F) PAGES: 235-241
  (G) DATE: spring 1992.

(ix) SEQUENCE DESCRIPTION: SEQ ID NO: 10:

Val Ala Ala Lys Ala Asn Arg Val Ala Asp Glu Ile Arg
1               5                   10
His Lys Arg Glu Lys Leu Glu
    15              20

(2) INFORMATION FOR SEQ ID NO:11:

(i) SEQUENCE CHARACTERISTICS:
    (A) LENGTH: 14 AMINO ACIDS
    (B) TYPE: AMINO ACID
    (D) TOPOLOGY: LINEAR (ii) MOLECULE TYPE: PEPTIDE (v) FRAGMENT TYPE: Whole peptide (ix) FEATURE:
    (A) NAME/KEY: Holst
    (B) LOCATION: Gastrin releasing peptide, whole peptide
    (C) IDENTIFICATION METHOD: by its lack of amphiphilicity or other structural similarity to melittin.
    (D) OTHER INFORMATION: melittin is the main component in honey bee toxin and is able to lyse red blood cells. This molecule is not a structural analogue of melittin or has any structural similarity and can therefore be used for control experiments.

(x) PUBLICATION INFORMATION:
    (A) AUTHORS: Wachinger, Michael, Saermark,Torben & Erfle,Volker.
    (B) TITLE: Influence of amphipathic peptides on the HIV-1 production in persistently infected T-lymphoma cells.
    (C) JOURNAL: FEBS letters
    (D) VOLUME: 309
    (E) ISSUE: 3
    (F) PAGES: 235-241
    (G) DATE: spring 1992.

(ix) SEQUENCE DESCRIPTION: SEQ ID NO: 11:

Phe Ala Glu Ser Gly Val Asp Thr Pro Val Phe Asn Ser Tyr
1               5                   10

(2) INFORMATION FOR SEQ ID NO:12:

(i) SEQUENCE CHARACTERISTICS:
    (A) LENGTH: 26 AMINO ACIDS
    (B) TYPE: AMINO ACID
    (D) TOPOLOGY: LINEAR (ii) MOLECULE TYPE: PEPTIDE (ix) FEATURE:
    (A) NAME/KEY: melittin 3
    (B) LOCATION: analogue of whole molecule
    (C) IDENTIFICATION METHOD: Modification of the C-terminus of native melittin, which was identified as an antiviral compound by experiments on HIV release from human LC5 cells and sequence similarity to gp41 from Human Immunodeficiency Virus (hiv).
    (D) OTHER INFORMATION: melittin is the main component in honey bee toxin and is able to lyse red blood cells. This analogue is a C-terminal modification prepared to study the importance of the structure of the C-terminal part of the molecule on HIV release.

(x) PUBLICATION INFORMATION:
  (A) AUTHORS: Wachinger, Michael, Saermark,Torben &
      Erfle,Volker.
  (B) TITLE: Influence of amphipathic peptides on the HIV-1
      production in persistently infected T-lymphoma cells.
  (C) JOURNAL: FEBS letters
  (D) VOLUME: 309
  (E) ISSUE: 3
  (F) PAGES: 235-241
  (G) DATE: september 14, 1992.

(ix) SEQUENCE DESCRIPTION: SEQ ID NO: 12:

Gly Ile Gly Ala Val Leu Lys Val Leu Thr Thr Gly Leu
1               5                   10

Pro Ala Leu Ile Ser Trp Ile Lys Arg Lys Arg Gly Gly
    15              20                  25

Having described our invention what we claim as new and desire to secure by Letters Patent is:

1. A method for inhibiting retroviral replication in mammalian cells, the method comprising:
    administering a therapeutically-effective amount of melittin (Seq. ID No. 1) or one or more structural analogues thereof (Seq. ID No. 2–8 or 12) whereby virus replication in the retroviral infected cells is inhibited and/or growth of the retroviral infected cells is inhibited.

2. A method as claimed in claim 1 wherein the administration includes a structural analogue of melittin, and wherein a Rauscher leukemia virus infection is treated.

3. A method as claimed in claim 1 and wherein the administration includes only Melittin and wherein a feline immunodeficiency virus infection or a Rauscher leukemia infection virus is treated.

4. A method as claimed in claim 1 and wherein a HIV infection is treated.

5. A method as claimed in claim 1 and wherein the structural analogues of melittin (Seq. ID No. 2–7 and 12) include an amphiphilic helix.

6. A method as claimed in claim 1 and wherein the structural analogue of melittin is Gly-Ile-Gly-Ala-Val-Leu-Lys-Val-Leu-Thr-Thr-Gly-Leu-Pro-Ala-Leu-Ile-Ser-Trp-Ile-Gly-Gly-Gly-Gly-Gly-Gly.

7. A method as claimed in claim 1 and wherein the structural analogues of melittin (Seq. ID No. 1) is Amfi 1 (Seq. ID No. 8).

8. A method for inhibiting retroviral replication in mammalian cells, the method comprising:
    administering a therapeutically-effective amount of melittin (Seq. ID No. 1) or a structural analogue thereof (Seq. ID No. 2–7 or 12) in the form of an agent selected from the group consisting of a hymenoptera venom; an active protein component of a hymenoptera venom; a polypeptide component of a hymenoptera venom; and mixtures of the foregoing; whereby virus replication in the retroviral infected mammalian cells is inhibited.

9. A method as claimed in claim 8 and wherein the agent is selected from the group consisting of honeybee venom; bumblebee venom; bald-faced hornet venom; active protein components of honeybee venom, bumblebee venom and bald face hornet venom, and mixtures thereof.

10. A method as in claim 9, and wherein the retroviral infection is HIV.

* * * * *

UNITED STATES PATENT AND TRADEMARK OFFICE
CERTIFICATE OF CORRECTION

PATENT NO. : 5,770,688
DATED : June 23, 1998
INVENTOR(S) : Torben Saemark & Volker Erfle It is certified that error appears in the above-indentified patent and that said Letters Patent is hereby corrected as shown below:

Col. 9, line 55: "120°C" should read --120°--.
Col. 35, Claim 6, line 2: "melittin is" should read --melittin (Seq ID No. 1)--.

Signed and Sealed this

Ninth Day of February, 1999

Attest:

Attesting Officer

Acting Commissioner of Patents and Trademarks